United States Patent
Nair et al.

(10) Patent No.: US 11,679,195 B2
(45) Date of Patent: Jun. 20, 2023

(54) THROMBUS ASPIRATION SYSTEM AND METHODS FOR CONTROLLING BLOOD LOSS

(71) Applicant: Contego Medical, Inc., Raleigh, NC (US)

(72) Inventors: Ajit Nair, Pleasanton, CA (US); Christopher R. Kilgus, Felton, CA (US); Ravish Sachar, Raleigh, NC (US)

(73) Assignee: Contego Medical, Inc., Raleigh, NC (US)

( * ) Notice: Subject to any disclaimer, the term of this patent is extended or adjusted under 35 U.S.C. 154(b) by 0 days.

(21) Appl. No.: 17/726,791

(22) Filed: Apr. 22, 2022

(65) Prior Publication Data

US 2022/0339339 A1    Oct. 27, 2022

Related U.S. Application Data

(60) Provisional application No. 63/180,291, filed on Apr. 27, 2021.

(51) Int. Cl.
*A61M 1/00* (2006.01)
*A61B 17/221* (2006.01)
(Continued)

(52) U.S. Cl.
CPC .............. *A61M 1/74* (2021.05); *A61B 17/22* (2013.01); *A61B 17/221* (2013.01); *A61F 2/011* (2020.05);
(Continued)

(58) Field of Classification Search
CPC ..... A61B 17/3203; A61B 17/22; A61B 17/34; A61B 2017/22079; A61M 1/00; A61M 1/74; A61M 1/75; A61F 2/011
See application file for complete search history.

(56) References Cited

U.S. PATENT DOCUMENTS 3,693,613 A * 9/1972 Kelman .............. A61F 9/00745
                                                          137/115.03
3,930,505 A     1/1976 Wallach
(Continued)

FOREIGN PATENT DOCUMENTS

CN        215386236 U  *  1/2022  ............. A61B 17/22
WO        2013064852 A1    5/2013
(Continued)

OTHER PUBLICATIONS

US 11,191,563 B2, 12/2021, Savastano et al. (withdrawn)
(Continued)

*Primary Examiner* — Scott J Medway
(74) *Attorney, Agent, or Firm* — Meunier Carlin & Curfman LLC

(57) ABSTRACT

Aspiration systems and methods for controlling blood loss during thrombus removal are disclosed herein. The systems include an aspiration catheter, an aspiration tubing, a receptacle for collecting aspirated blood, a vacuum line coupled to the receptacle, and a sensor configured to measure a flow parameter associated with a liquid within an aspiration lumen. The systems further include a regulator configured to adjust a vacuum pressure within the vacuum line, and a vacuum controller operably coupled to the sensor and the regulator. The vacuum controller is configured to receive the flow parameter from the sensor, compare the flow parameter to a target range for the flow parameter, and send an automatic control signal to the regulator based on a comparison of the flow parameter to the target range. The automatic control signal causes the regulator to adjust the vacuum pressure within the vacuum line.

27 Claims, 16 Drawing Sheets

(51) Int. Cl.
*A61F 2/01* (2006.01)
*A61B 17/22* (2006.01)
*A61M 25/00* (2006.01)
*A61B 17/00* (2006.01)

(52) U.S. Cl.
CPC ............... *A61M 1/60* (2021.05); *A61M 1/73* (2021.05); *A61M 1/7415* (2021.05); *A61M 1/76* (2021.05); *A61M 25/0068* (2013.01); *A61B 2017/00778* (2013.01); *A61B 2017/22079* (2013.01); *A61B 2217/005* (2013.01); *A61M 2205/15* (2013.01); *A61M 2205/3334* (2013.01)

(56) References Cited

U.S. PATENT DOCUMENTS

| | | | |
|---|---|---|---|
| 4,244,230 A * | 1/1981 | Bauer | G01F 1/20 73/861.19 |
| 4,332,560 A | 6/1982 | Rait | |
| 4,460,361 A | 7/1984 | Nichols | |
| 4,654,029 A * | 3/1987 | D'Antonio | A61M 1/742 600/584 |
| 4,735,606 A * | 4/1988 | Davison | A61M 1/85 604/35 |
| 4,935,005 A | 6/1990 | Haines | |
| 5,094,961 A | 3/1992 | DelValle et al. | |
| 5,195,995 A * | 3/1993 | Walker | A61M 1/61 604/319 |
| 5,201,703 A * | 4/1993 | Gentelia | A61M 1/0011 604/319 |
| 5,536,242 A | 7/1996 | Willard | |
| 5,606,968 A | 3/1997 | Mang | |
| 5,897,524 A | 4/1999 | Wortrich et al. | |
| 5,941,869 A * | 8/1999 | Patterson | A61B 17/320758 606/198 |
| 6,013,046 A | 1/2000 | Maaskamp et al. | |
| 6,039,715 A | 3/2000 | Mackool | |
| 6,055,458 A | 4/2000 | Cochran et al. | |
| 6,258,053 B1 | 7/2001 | Mackool | |
| 6,290,689 B1 | 9/2001 | Delaney et al. | |
| 6,319,223 B1 | 11/2001 | Wortrich et al. | |
| 6,514,268 B2 | 2/2003 | Finlay et al. | |
| 6,629,646 B1 | 10/2003 | Ivri | |
| 6,663,613 B1 | 12/2003 | Evans et al. | |
| 6,730,063 B2 | 5/2004 | Delaney et al. | |
| 6,773,445 B2 | 8/2004 | Finlay et al. | |
| 6,790,196 B2 | 9/2004 | Kokate et al. | |
| 6,887,220 B2 | 5/2005 | Kataishi et al. | |
| 6,926,208 B2 | 8/2005 | Ivri | |
| 6,929,633 B2 | 8/2005 | Evans et al. | |
| 6,979,293 B2 | 12/2005 | Hansmann et al. | |
| 7,004,931 B2 | 2/2006 | Hogendijk | |
| 7,108,197 B2 | 9/2006 | Ivri | |
| 7,141,045 B2 | 11/2006 | Johansson et al. | |
| 7,160,268 B2 | 1/2007 | Darnell et al. | |
| 7,244,250 B2 | 7/2007 | Miki et al. | |
| 7,250,042 B2 | 7/2007 | Rauker et al. | |
| 7,276,052 B2 * | 10/2007 | Kobayashi | A61M 1/80 604/319 |
| 7,276,060 B2 | 10/2007 | Madden | |
| 7,309,334 B2 | 12/2007 | von Hoffmann | |
| 7,422,579 B2 * | 9/2008 | Wahr | A61B 17/12109 604/509 |
| 7,491,192 B2 | 2/2009 | Di Fiore | |
| 7,608,063 B2 | 10/2009 | Le et al. | |
| 7,655,016 B2 | 2/2010 | Demarais et al. | |
| 7,666,161 B2 | 2/2010 | Nash et al. | |
| 7,674,272 B2 | 3/2010 | Torrance et al. | |
| 7,713,231 B2 | 5/2010 | Wulfman et al. | |
| 7,713,235 B2 | 5/2010 | Torrance et al. | |
| 7,717,934 B2 | 5/2010 | Knsleika | |
| 7,736,355 B2 | 6/2010 | Itou et al. | |
| 7,762,995 B2 | 7/2010 | Eversull et al. | |
| 7,763,010 B2 | 7/2010 | Evans et al. | |
| 7,780,694 B2 | 8/2010 | Palmer et al. | |
| 7,792,647 B1 | 9/2010 | Ding et al. | |
| 7,842,009 B2 | 11/2010 | Torrance et al. | |
| 7,842,010 B2 | 11/2010 | Bonnette et al. | |
| 7,887,510 B2 * | 2/2011 | Karpowicz | A61M 1/74 604/118 |
| 7,918,822 B2 | 4/2011 | Kumar et al. | |
| 7,931,659 B2 | 4/2011 | Bose et al. | |
| 7,935,077 B2 | 5/2011 | Thor et al. | |
| 7,938,820 B2 | 5/2011 | Webster et al. | |
| 7,942,852 B2 | 5/2011 | Mas et al. | |
| 7,947,012 B2 | 5/2011 | Spurchise et al. | |
| 7,959,608 B2 | 6/2011 | Nash et al. | |
| 7,976,528 B2 | 7/2011 | Nash et al. | |
| 7,981,128 B2 | 7/2011 | To et al. | |
| 7,998,104 B2 | 8/2011 | Chang | |
| 8,002,728 B2 | 8/2011 | Chang | |
| 8,007,506 B2 | 8/2011 | To et al. | |
| 8,012,117 B2 | 9/2011 | Bonnette et al. | |
| 8,021,351 B2 | 9/2011 | Boldenow et al. | |
| 8,052,640 B2 | 11/2011 | Fiorella et al. | |
| 8,057,439 B2 | 11/2011 | Di Fiore | |
| 8,066,677 B2 | 11/2011 | Lnnn et al. | |
| 8,066,757 B2 | 11/2011 | Ferrera et al. | |
| 8,070,694 B2 | 12/2011 | Galdonik et al. | |
| 8,070,762 B2 | 12/2011 | Escudero et al. | |
| 8,070,791 B2 | 12/2011 | Ferrera et al. | |
| 8,088,103 B2 | 1/2012 | Teeslink et al. | |
| 8,088,140 B2 | 1/2012 | Ferrera et al. | |
| 8,114,106 B2 | 2/2012 | Straub | |
| 8,137,377 B2 | 3/2012 | Palmer et al. | |
| 8,142,442 B2 | 3/2012 | Palmer et al. | |
| 8,157,760 B2 | 4/2012 | Criado et al. | |
| 8,162,878 B2 | 4/2012 | Bonnette et al. | |
| 8,231,600 B2 | 7/2012 | von Hoffmann | |
| 8,252,020 B2 | 8/2012 | Hauser et al. | |
| 8,262,611 B2 | 9/2012 | Teeslink et al. | |
| 8,298,210 B2 | 10/2012 | Provost-Tine et al. | |
| 8,303,538 B2 | 11/2012 | Bonnette et al. | |
| 8,317,748 B2 | 11/2012 | Fiorella et al. | |
| 8,323,240 B2 | 12/2012 | Wulfman et al. | |
| 8,337,516 B2 | 12/2012 | Escudero et al. | |
| 8,361,105 B2 | 1/2013 | Adams et al. | |
| 8,366,663 B2 | 2/2013 | Fiorella et al. | |
| 8,366,735 B2 | 2/2013 | Bose et al. | |
| 8,388,582 B2 | 3/2013 | Enbanks et al. | |
| 8,388,628 B2 | 3/2013 | Eversull et al. | |
| 8,398,589 B2 | 3/2013 | Teeslink et al. | |
| 8,405,568 B2 | 3/2013 | Knudsen et al. | |
| 8,430,837 B2 | 4/2013 | Jenson et al. | |
| 8,430,840 B2 | 4/2013 | Nazarifar et al. | |
| 8,435,228 B2 | 5/2013 | Wulfman et al. | |
| 8,439,878 B2 | 5/2013 | Bonnette et al. | |
| 8,444,661 B2 | 5/2013 | Nair et al. | |
| 8,460,312 B2 | 6/2013 | Bose et al. | |
| 8,465,467 B2 | 6/2013 | Gao | |
| 8,469,970 B2 | 6/2013 | Diamant et al. | |
| 8,475,484 B2 | 7/2013 | Wulfman et al. | |
| 8,500,683 B2 | 8/2013 | Constantz et al. | |
| 8,529,491 B2 | 9/2013 | Beiriger | |
| 8,535,290 B2 | 9/2013 | Evans et al. | |
| 8,545,432 B2 | 10/2013 | Renati et al. | |
| 8,545,514 B2 | 10/2013 | Ferrera | |
| 8,562,555 B2 | 10/2013 | MacMahon et al. | |
| 8,568,432 B2 | 10/2013 | Straub | |
| 8,574,262 B2 | 11/2013 | Ferrera et al. | |
| 8,585,713 B2 | 11/2013 | Ferrera et al. | |
| 8,591,453 B2 | 11/2013 | Stubkjaer et al. | |
| 8,628,549 B2 | 1/2014 | To et al. | |
| 8,647,355 B2 | 2/2014 | Escudero et al. | |
| 8,652,086 B2 | 2/2014 | Gerg et al. | |
| 8,657,785 B2 | 2/2014 | Torrance et al. | |
| 8,668,665 B2 | 3/2014 | Gerg et al. | |
| 8,679,142 B2 | 3/2014 | Slee et al. | |
| 8,679,150 B1 | 3/2014 | Janardhan et al. | |
| 8,690,907 B1 | 4/2014 | Janardhan et al. | |
| 8,696,622 B2 | 4/2014 | Fiorella et al. | |
| 8,702,652 B2 | 4/2014 | Fiorella et al. | |

(56) References Cited

U.S. PATENT DOCUMENTS

| | | |
|---|---|---|
| 8,715,220 B2 | 5/2014 | Gerg et al. |
| 8,715,314 B1 | 5/2014 | Janardhan et al. |
| 8,715,315 B1 | 5/2014 | Janardhan et al. |
| 8,715,316 B1 | 5/2014 | Janardhan et al. |
| 8,715,317 B1 | 5/2014 | Janardhan et al. |
| 8,721,676 B1 | 5/2014 | Janardhan et al. |
| 8,721,677 B1 | 5/2014 | Janardhan et al. |
| 8,728,116 B1 | 5/2014 | Janardhan et al. |
| 8,728,117 B1 | 5/2014 | Janardhan et al. |
| 8,733,618 B1 | 5/2014 | Janardhan et al. |
| 8,735,777 B1 | 5/2014 | Janardhan et al. |
| 8,747,432 B1 | 6/2014 | Janardhan et al. |
| 8,753,371 B1 | 6/2014 | Janardhan et al. |
| 8,758,325 B2 | 6/2014 | Webster et al. |
| 8,764,724 B2 | 7/2014 | Itou et al. |
| 8,783,151 B1 | 7/2014 | Janardhan et al. |
| 8,784,355 B2 | 7/2014 | Criado et al. |
| 8,784,434 B2 | 7/2014 | Rosenbluth et al. |
| 8,784,446 B1 | 7/2014 | Janardhan et al. |
| 8,789,452 B1 | 7/2014 | Janardhan et al. |
| 8,790,365 B1 | 7/2014 | Janardhan et al. |
| 8,795,330 B1 | 8/2014 | Janardhan et al. |
| 8,801,749 B2 | 8/2014 | Adams et al. |
| 8,803,030 B1 | 8/2014 | Janardhan et al. |
| 8,813,625 B1 | 8/2014 | Janardhan et al. |
| 8,814,892 B2 | 8/2014 | Galdonik et al. |
| 8,816,247 B1 | 8/2014 | Janardhan et al. |
| 8,828,045 B1 | 9/2014 | Janardhan et al. |
| 8,845,678 B1 | 9/2014 | Janardhan et al. |
| 8,845,679 B1 | 9/2014 | Janardhan et al. |
| 8,852,219 B2 | 10/2014 | Wulfman et al. |
| 8,852,227 B1 | 10/2014 | Janardhan et al. |
| 8,859,934 B1 | 10/2014 | Janardhan et al. |
| 8,863,631 B1 | 10/2014 | Janardhan et al. |
| 8,866,049 B1 | 10/2014 | Janardhan et al. |
| 8,869,670 B1 | 10/2014 | Janardhan et al. |
| 8,870,805 B2 | 10/2014 | Chang |
| 8,870,824 B2 | 10/2014 | Kusakabe |
| 8,870,901 B1 | 10/2014 | Janardhan et al. |
| 8,870,910 B1 | 10/2014 | Janardhan et al. |
| 8,872,068 B1 | 10/2014 | Janardhan et al. |
| 8,882,797 B2 | 11/2014 | Janardhan et al. |
| 8,888,801 B2 | 11/2014 | To et al. |
| 8,895,891 B2 | 11/2014 | Janardhan et al. |
| 8,900,179 B2 | 12/2014 | Jenson et al. |
| 8,900,257 B2 | 12/2014 | Straub et al. |
| 8,904,914 B2 | 12/2014 | Janardhan et al. |
| 8,910,555 B2 | 12/2014 | Janardhan et al. |
| 8,920,402 B2 | 12/2014 | Nash et al. |
| 8,920,448 B2 | 12/2014 | To et al. |
| 8,926,680 B2 | 1/2015 | Ferrera et al. |
| 8,932,320 B1 | 1/2015 | Janardhan et al. |
| 8,932,321 B1 | 1/2015 | Janardhan et al. |
| 8,939,931 B2 | 1/2015 | von Hoffmann |
| 8,940,003 B2 | 1/2015 | Slee et al. |
| 8,945,143 B2 | 2/2015 | Ferrera et al. |
| 8,945,172 B2 | 2/2015 | Ferrera et al. |
| 8,951,224 B2 | 2/2015 | Wulfman et al. |
| 8,956,386 B2 | 2/2015 | Hauser et al. |
| 8,970,384 B2 | 3/2015 | Yodfat et al. |
| 8,986,241 B2 | 3/2015 | Evans et al. |
| 8,998,843 B2 | 4/2015 | Bonnette et al. |
| 9,011,364 B2 | 4/2015 | Criado et al. |
| 9,011,467 B2 | 4/2015 | Garrison et al. |
| 9,017,309 B2 | 4/2015 | Tanikawa et al. |
| 9,039,715 B2 | 5/2015 | Diamant et al. |
| 9,050,127 B2 | 6/2015 | Bonnette et al. |
| 9,055,951 B2 | 6/2015 | Deshpande |
| 9,055,963 B2 | 6/2015 | Henkes et al. |
| 9,072,540 B2 | 7/2015 | Jarnagin et al. |
| 9,078,682 B2 | 7/2015 | Lenker et al. |
| 9,095,371 B2 | 8/2015 | Escudero et al. |
| 9,113,936 B2 | 8/2015 | Look et al. |
| 9,119,656 B2 | 9/2015 | Leynov et al. |
| 9,125,728 B2 | 9/2015 | Angel et al. |
| 9,126,018 B1 | 9/2015 | Garrison |
| 9,138,527 B2 | 9/2015 | Renati et al. |
| 9,149,568 B2 | 10/2015 | Gerg et al. |
| 9,161,765 B2 | 10/2015 | Thor et al. |
| 9,161,766 B2 | 10/2015 | Slee et al. |
| 9,179,909 B2 | 11/2015 | Garrison et al. |
| 9,179,931 B2 | 11/2015 | Janardhan et al. |
| 9,179,995 B2 | 11/2015 | Janardhan et al. |
| 9,186,487 B2 | 11/2015 | Dubrul et al. |
| 9,198,679 B2 | 12/2015 | To et al. |
| 9,198,687 B2 | 12/2015 | Fulkerson et al. |
| 9,220,522 B2 | 12/2015 | Fulkerson et al. |
| 9,238,122 B2 | 1/2016 | Malhi et al. |
| 9,239,049 B2 | 1/2016 | Jarnagin et al. |
| 9,241,699 B1 | 1/2016 | Kume et al. |
| 9,248,221 B2 | 2/2016 | Look et al. |
| 9,259,215 B2 | 2/2016 | Chou et al. |
| 9,259,237 B2 | 2/2016 | Quick et al. |
| 9,265,512 B2 | 2/2016 | Garrison et al. |
| 9,282,989 B2 | 3/2016 | Boukhny et al. |
| 9,283,040 B2 * | 3/2016 | Hendrick ............ A61B 18/245 |
| 9,295,373 B2 | 3/2016 | Torrance et al. |
| 9,301,829 B2 | 4/2016 | Rauker et al. |
| 9,308,016 B2 | 4/2016 | Escudero et al. |
| 9,308,315 B2 | 4/2016 | Stubkjaer et al. |
| 9,314,263 B2 | 4/2016 | Escudero et al. |
| 9,314,324 B2 | 4/2016 | Janardhan et al. |
| 9,320,532 B2 | 4/2016 | Ferrera et al. |
| 9,332,998 B2 | 5/2016 | Ray et al. |
| 9,332,999 B2 | 5/2016 | Ray et al. |
| 9,333,007 B2 | 5/2016 | Escudero et al. |
| 9,375,223 B2 | 6/2016 | Wallace |
| 9,387,098 B2 | 7/2016 | Ferrera et al. |
| 9,399,118 B2 | 7/2016 | Kume et al. |
| 9,408,620 B2 | 8/2016 | Rosenbluth et al. |
| 9,408,626 B2 | 8/2016 | Tekulve |
| 9,408,964 B2 | 8/2016 | Breiter et al. |
| 9,421,080 B2 | 8/2016 | Angel et al. |
| 9,427,300 B2 | 8/2016 | Angel et al. |
| 9,433,427 B2 | 9/2016 | Look et al. |
| 9,445,828 B2 | 9/2016 | Turjman et al. |
| 9,445,943 B2 | 9/2016 | Wilson et al. |
| 9,463,035 B1 | 10/2016 | Greenhalgh et al. |
| 9,492,192 B2 | 11/2016 | To et al. |
| 9,492,637 B2 | 11/2016 | Garrison et al. |
| 9,498,604 B2 | 11/2016 | Dubrul et al. |
| 9,510,854 B2 | 12/2016 | Mallaby |
| 9,522,258 B2 | 12/2016 | Tekulve |
| 9,526,504 B2 | 12/2016 | Chang |
| 9,526,864 B2 | 12/2016 | Quick |
| 9,526,865 B2 | 12/2016 | Quick |
| 9,526,874 B2 | 12/2016 | Teeslink et al. |
| 9,526,922 B2 | 12/2016 | Hossack et al. |
| 9,532,792 B2 | 1/2017 | Galdonik et al. |
| 9,539,022 B2 | 1/2017 | Bowman |
| 9,549,850 B2 | 1/2017 | Sorensen et al. |
| 9,554,822 B2 | 1/2017 | Consigny |
| 9,561,345 B2 | 2/2017 | Garrison et al. |
| 9,592,068 B2 | 3/2017 | Janardhan et al. |
| 9,597,101 B2 | 3/2017 | Galdonik et al. |
| 9,629,654 B2 | 4/2017 | Andersen |
| 9,649,437 B2 | 5/2017 | Eubanks et al. |
| 9,655,633 B2 | 5/2017 | Leynov et al. |
| 9,655,755 B2 | 5/2017 | Chou et al. |
| 9,656,043 B2 | 5/2017 | Bhagchandani et al. |
| 9,662,118 B2 | 5/2017 | Chang |
| 9,662,129 B2 | 5/2017 | Galdonik et al. |
| 9,662,137 B2 | 5/2017 | Jenson et al. |
| 9,662,480 B2 | 5/2017 | Kume et al. |
| 9,668,767 B2 | 6/2017 | To et al. |
| 9,669,191 B2 | 6/2017 | Chou et al. |
| 9,675,376 B2 | 6/2017 | To et al. |
| 9,681,882 B2 | 6/2017 | Garrison et al. |
| 9,693,898 B2 | 7/2017 | Farley et al. |
| 9,700,332 B2 | 7/2017 | Marchand et al. |
| 9,700,347 B2 | 7/2017 | Shiber |
| 9,707,002 B2 | 7/2017 | Henkes et al. |
| 9,717,519 B2 | 8/2017 | Rosenbluth et al. |
| 9,731,065 B2 | 8/2017 | Bourne et al. |

(56) References Cited

U.S. PATENT DOCUMENTS

| | | | |
|---|---|---|---|
| 9,737,328 B2 | 8/2017 | Bonnette et al. |
| 9,750,517 B2 | 9/2017 | Agrawal |
| 9,750,524 B2 | 9/2017 | Janardhan et al. |
| 9,775,964 B2 | 10/2017 | Eubanks et al. |
| 9,789,242 B2 | 10/2017 | Criado et al. |
| 9,801,642 B2 | 10/2017 | Thor et al. |
| 9,801,643 B2 | 10/2017 | Hansen et al. |
| 9,801,644 B2 | 10/2017 | Ulm, III |
| 9,808,266 B2 | 11/2017 | Ray et al. |
| 9,808,271 B2 | 11/2017 | Ulm, III |
| 9,808,277 B2 | 11/2017 | Nash et al. |
| 9,814,478 B2 | 11/2017 | Ulm, III |
| 9,820,761 B2 | 11/2017 | Garrison et al. |
| 9,820,764 B2 | 11/2017 | Ulm, III |
| 9,826,998 B2 | 11/2017 | Ulm, III |
| 9,833,251 B2 | 12/2017 | Janardhan et al. |
| 9,833,253 B1 | 12/2017 | Ulm, III |
| 9,833,257 B2 | 12/2017 | Bonnette et al. |
| 9,833,555 B2 | 12/2017 | Criado et al. |
| 9,839,506 B2 | 12/2017 | Ulm, III |
| 9,839,771 B2 | 12/2017 | Eversull et al. |
| 9,844,387 B2 | 12/2017 | Marchand et al. |
| 9,848,881 B2 | 12/2017 | Sutton et al. |
| 9,848,975 B2 | 12/2017 | Nash et al. |
| 9,855,375 B2 | 1/2018 | Charron et al. |
| 9,861,783 B2 | 1/2018 | Garrison et al. |
| 9,878,076 B2 | 1/2018 | Gulcher et al. |
| 9,883,877 B2 | 2/2018 | Look et al. |
| 9,895,158 B2 | 2/2018 | Dixon et al. |
| 9,895,473 B2 | 2/2018 | Look et al. |
| 9,901,435 B2 | 2/2018 | Janardhan et al. |
| 9,907,567 B2 | 3/2018 | Shiber |
| 9,913,936 B2 | 3/2018 | Look et al. |
| 9,925,315 B2 | 3/2018 | Eubanks et al. |
| 9,931,166 B2 | 4/2018 | Sauro et al. |
| 9,931,447 B2 | 4/2018 | Layser et al. |
| 9,943,321 B2 | 4/2018 | Nita |
| 9,943,668 B2 | 4/2018 | Jahrmarkt |
| 9,955,987 B2 | 5/2018 | Ulm, III |
| 9,962,177 B2 | 5/2018 | Ulm, III |
| 9,962,288 B2 | 5/2018 | Yalamanchili |
| 9,987,028 B2 | 6/2018 | Lowinger et al. |
| 10,004,531 B2 | 6/2018 | Rosenbluth et al. |
| 10,010,657 B2 | 7/2018 | Torrance et al. |
| 10,016,211 B2 | 7/2018 | Ferrera et al. |
| 10,016,266 B2 | 7/2018 | Hauser |
| 10,022,139 B2 | 7/2018 | Kobayashi et al. |
| 10,039,906 B2 | 8/2018 | Kume et al. |
| 10,045,790 B2 | 8/2018 | Cox et al. |
| 10,058,339 B2 | 8/2018 | Galdonik et al. |
| 10,064,643 B2 | 9/2018 | Malhi et al. |
| 10,085,864 B2 | 10/2018 | Chou et al. |
| 10,098,651 B2 | 10/2018 | Marchand et al. |
| 10,098,724 B2 | 10/2018 | Adams et al. |
| 10,117,669 B2 | 11/2018 | Kobayashi et al. |
| 10,117,670 B2 | 11/2018 | Kobayashi et al. |
| 10,137,034 B2 | 11/2018 | Heeren |
| 10,143,489 B2 | 12/2018 | Kobayashi et al. |
| 10,149,692 B2 | 12/2018 | Turjman et al. |
| 10,149,698 B2 | 12/2018 | Wulfman et al. |
| 10,154,853 B2 | 12/2018 | To et al. |
| 10,154,854 B2 | 12/2018 | To et al. |
| 10,179,224 B2 | 1/2019 | Yang et al. |
| 10,182,940 B2 | 1/2019 | Chandrakant et al. |
| 10,183,145 B2 | 1/2019 | Yang et al. |
| 10,183,146 B2 | 1/2019 | Yang et al. |
| 10,183,147 B2 | 1/2019 | Yang et al. |
| 10,188,399 B2 | 1/2019 | Chang |
| 10,188,409 B2 | 1/2019 | Smalling |
| 10,192,230 B2 | 1/2019 | Look et al. |
| 10,201,359 B2 | 2/2019 | Fiorella et al. |
| 10,213,582 B2 | 2/2019 | Garrison et al. |
| 10,219,814 B2 | 3/2019 | Feltyberger et al. |
| 10,226,263 B2 | 3/2019 | Look et al. |
| 10,226,268 B2 | 3/2019 | Ulm, III |
| 10,226,275 B2 | 3/2019 | Eseudero et al. |
| 10,226,563 B2 | 3/2019 | Garrison et al. |
| 10,226,598 B2 | 3/2019 | Chou et al. |
| 10,238,406 B2 | 3/2019 | Cox et al. |
| 10,238,853 B2 | 3/2019 | Kume et al. |
| 10,251,739 B2 | 4/2019 | Janardhan et al. |
| 10,258,358 B2 | 4/2019 | Ulm, III |
| 10,271,864 B2 | 4/2019 | Greenhalgh et al. |
| D847,864 S | 5/2019 | Janardhan et al. |
| D847,865 S | 5/2019 | Janardhan et al. |
| D847,866 S | 5/2019 | Janardhan et al. |
| 10,278,719 B2 | 5/2019 | Ulm, III |
| 10,278,861 B2 | 5/2019 | Bourne et al. |
| 10,285,720 B2 | 5/2019 | Gilvarry et al. |
| 10,299,824 B2 | 5/2019 | Walzman |
| D850,490 S | 6/2019 | Janardhan et al. |
| 10,307,242 B2 | 6/2019 | Walzman |
| 10,314,608 B2 | 6/2019 | Jenson et al. |
| 10,314,609 B2 | 6/2019 | Bonnette et al. |
| 10,314,684 B2 | 6/2019 | Walzman |
| 10,314,953 B2 | 6/2019 | Ovehinnikov et al. |
| 10,321,925 B2 | 6/2019 | Ulm, III |
| 10,327,790 B2 | 6/2019 | Garrison et al. |
| 10,335,186 B2 | 7/2019 | Rosenbluth et al. |
| 10,335,260 B2 | 7/2019 | Janardhan et al. |
| 10,342,571 B2 | 7/2019 | Marchand et al. |
| 10,342,655 B2 | 7/2019 | Janardhan et al. |
| 10,349,960 B2 | 7/2019 | Quick |
| 10,357,242 B2 | 7/2019 | Garrison et al. |
| 10,357,266 B2 | 7/2019 | Ulm, III |
| 10,363,054 B2 | 7/2019 | Vale et al. |
| 10,369,270 B2 | 8/2019 | Stubkjaer et al. |
| 10,369,346 B2 | 8/2019 | Ryan et al. |
| 10,376,678 B2 | 8/2019 | Levine |
| 10,376,685 B2 | 8/2019 | Angel et al. |
| 10,383,644 B2 | 8/2019 | Molaei et al. |
| 10,384,034 B2 | 8/2019 | Garrison et al. |
| 10,390,926 B2 | 8/2019 | Janardhan et al. |
| 10,398,595 B2 | 9/2019 | Zacharias |
| 10,405,924 B2 * | 9/2019 | Bowe .................. A61B 18/245 |
| 10,413,310 B2 | 9/2019 | Ferrera et al. |
| 10,420,572 B2 | 9/2019 | Ulm, III |
| 10,426,511 B2 | 10/2019 | Hehrlein |
| 10,426,885 B2 | 10/2019 | Criado et al. |
| 10,441,301 B2 | 10/2019 | Vale et al. |
| 10,441,745 B2 | 10/2019 | Yang et al. |
| 10,448,969 B2 | 10/2019 | Sutton et al. |
| 10,456,151 B2 | 10/2019 | Slee et al. |
| 10,456,555 B2 * | 10/2019 | Garrison .............. A61B 17/221 |
| 10,463,351 B2 | 11/2019 | Merk et al. |
| 10,463,386 B2 | 11/2019 | Ogle et al. |
| 10,463,468 B2 | 11/2019 | Janardhan et al. |
| 10,470,926 B2 | 11/2019 | Zacharias |
| 10,471,233 B2 | 11/2019 | Garrison et al. |
| 10,485,551 B2 | 11/2019 | Turjman et al. |
| 10,485,564 B2 | 11/2019 | Goyal |
| 10,485,565 B2 | 11/2019 | Galdonik et al. |
| 10,485,952 B2 | 11/2019 | Garrison et al. |
| 10,492,805 B2 | 12/2019 | Culbert et al. |
| 10,492,809 B2 | 12/2019 | Ulm, III |
| 10,499,944 B2 | 12/2019 | Mallaby |
| 10,517,633 B2 | 12/2019 | Nash et al. |
| 10,524,811 B2 | 1/2020 | Marchand et al. |
| 10,531,882 B2 | 1/2020 | Anand et al. |
| 10,531,883 B1 * | 1/2020 | Deville .................. A61M 1/79 |
| 10,537,471 B2 | 1/2020 | Look et al. |
| 10,561,440 B2 | 2/2020 | Look et al. |
| 10,569,049 B2 | 2/2020 | Garrison et al. |
| 10,588,655 B2 | 3/2020 | Rosenbluth et al. |
| 10,588,656 B2 | 3/2020 | Trosper et al. |
| 10,595,818 B2 | 3/2020 | Levine |
| 10,603,415 B2 | 3/2020 | Look et al. |
| 10,610,256 B2 | 4/2020 | Bowman |
| 10,617,435 B2 | 4/2020 | Vale et al. |
| 10,617,562 B2 | 4/2020 | Bourne et al. |
| 10,624,659 B2 | 4/2020 | Gamba et al. |
| 10,632,245 B2 | 4/2020 | Enbanks et al. |
| 10,646,239 B2 | 5/2020 | Garrison et al. |
| 10,653,434 B1 | 5/2020 | Yang et al. |

(56) References Cited

U.S. PATENT DOCUMENTS

| | | | |
|---|---|---|---|
| 10,661,053 | B2 | 5/2020 | Yang et al. |
| 10,682,152 | B2 | 6/2020 | Vale et al. |
| 10,690,127 | B2 | 6/2020 | Ochoa |
| 10,695,159 | B2 | 6/2020 | Hauser |
| 10,702,292 | B2 | 7/2020 | Look et al. |
| 10,702,415 | B2* | 7/2020 | Charles .................. A61M 1/77 |
| 10,702,634 | B2* | 7/2020 | Luxon .................. A61M 1/742 |
| 10,709,466 | B2 | 7/2020 | Bowman et al. |
| 10,709,832 | B2 | 7/2020 | Criado et al. |
| 10,716,482 | B2 | 7/2020 | Anderson et al. |
| 10,716,583 | B2 | 7/2020 | Look et al. |
| 10,716,880 | B2 | 7/2020 | Culbert et al. |
| 10,716,915 | B2 | 7/2020 | Ogle et al. |
| 10,722,238 | B2 | 7/2020 | Sutton et al. |
| 10,722,239 | B2 | 7/2020 | Chang |
| 10,722,251 | B2 | 7/2020 | Garrison et al. |
| 10,722,253 | B2 | 7/2020 | DeVille et al. |
| 10,722,255 | B2 | 7/2020 | Leaker et al. |
| 10,729,455 | B2 | 8/2020 | Goyal et al. |
| 10,743,893 | B2 | 8/2020 | Garrison et al. |
| 10,751,159 | B2 | 8/2020 | Janardhan et al. |
| 10,772,644 | B2 | 9/2020 | Feltyberger et al. |
| 10,772,649 | B2 | 9/2020 | Hansen et al. |
| 10,779,835 | B2 | 9/2020 | Chang |
| 10,779,855 | B2 | 9/2020 | Garrison |
| 10,786,270 | B2 | 9/2020 | Yang et al. |
| 10,792,056 | B2 | 10/2020 | Vale et al. |
| 10,799,331 | B2 | 10/2020 | Hauser |
| 10,828,061 | B2 | 11/2020 | Bonnette et al. |
| 10,835,257 | B2 | 11/2020 | Ferrera et al. |
| 10,835,271 | B2 | 11/2020 | Ma |
| 10,835,272 | B2 | 11/2020 | Yang et al. |
| 10,835,278 | B2 | 11/2020 | Wilke et al. |
| 10,835,711 | B2 | 11/2020 | Yang et al. |
| 10,864,351 | B2 | 12/2020 | Garrison et al. |
| 10,864,357 | B2 | 12/2020 | Kume et al. |
| 10,869,956 | B2 | 12/2020 | Torrance et al. |
| 10,874,410 | B2 | 12/2020 | Scarpine et al. |
| 10,874,411 | B2 | 12/2020 | Ngnyen et al. |
| 10,888,346 | B2 | 1/2021 | Ulm, III |
| 10,893,881 | B2 | 1/2021 | Dixon et al. |
| 10,893,978 | B2 | 1/2021 | Sawicz |
| 10,905,448 | B2 | 2/2021 | Machi |
| 10,912,577 | B2 | 2/2021 | Marchand et al. |
| 10,912,871 | B2 | 2/2021 | Gulcher et al. |
| 10,922,704 | B2 | 2/2021 | Look et al. |
| 10,932,797 | B2 | 3/2021 | Thomas |
| 10,932,810 | B2 | 3/2021 | Malhi et al. |
| 10,939,931 | B2 | 3/2021 | Grandfield et al. |
| 10,952,757 | B2 | 3/2021 | Galdonik et al. |
| 10,952,882 | B2 | 3/2021 | Chou et al. |
| 10,959,750 | B2 | 3/2021 | Wallace |
| 10,960,178 | B2 | 3/2021 | Savastano et al. |
| 10,993,731 | B2 | 5/2021 | Leynov et al. |
| 11,013,523 | B2 | 5/2021 | Arad Hadar |
| 11,026,709 | B2 | 6/2021 | Greenhalgh et al. |
| 11,027,104 | B2 | 6/2021 | Kume et al. |
| 11,051,832 | B2 | 7/2021 | Look et al. |
| 11,051,978 | B2 | 7/2021 | Heeren et al. |
| 11,058,445 | B2 | 7/2021 | Cox et al. |
| 11,058,451 | B2 | 7/2021 | Marchand et al. |
| 11,065,018 | B2 | 7/2021 | Buck et al. |
| 11,077,288 | B2 | 8/2021 | Govari |
| 11,083,485 | B2 | 8/2021 | Kobayashi et al. |
| 11,083,559 | B2 | 8/2021 | Kobayashi et al. |
| 11,090,070 | B2 | 8/2021 | Fiorella et al. |
| 11,090,071 | B2 | 8/2021 | Girdhar et al. |
| 11,090,466 | B1 | 8/2021 | Nieholson |
| 11,096,703 | B2 | 8/2021 | Panian |
| 11,096,712 | B2 | 8/2021 | Teigen et al. |
| 11,096,715 | B2 | 8/2021 | Hatta et al. |
| 11,103,265 | B2 | 8/2021 | Wallace et al. |
| 11,116,528 | B2 | 9/2021 | Wallace |
| 11,123,090 | B2 | 9/2021 | Yang et al. |
| 11,129,629 | B2 | 9/2021 | Welch et al. |
| 11,147,571 | B2 | 10/2021 | Cox et al. |
| 11,147,949 | B2 | 10/2021 | Yang et al. |
| 11,160,570 | B2 | 11/2021 | Skujins et al. |
| 11,160,571 | B2 | 11/2021 | Nguyen et al. |
| 11,160,572 | B2 | 11/2021 | Ulm, III |
| 11,185,623 | B2 | 11/2021 | Ovehinnikov et al. |
| 11,185,664 | B2 | 11/2021 | Garrison et al. |
| 11,191,558 | B2 | 12/2021 | Nguyen et al. |
| 11,197,683 | B1 | 12/2021 | Teigen et al. |
| 11,197,977 | B2 | 12/2021 | Mullins et al. |
| 11,207,096 | B2 | 12/2021 | To et al. |
| 11,207,456 | B2 | 12/2021 | Charron et al. |
| 11,224,458 | B2 | 1/2022 | Savastano et al. |
| 11,224,721 | B2 | 1/2022 | Garrison et al. |
| 11,229,445 | B2 | 1/2022 | Ogle |
| 11,229,451 | B2 | 1/2022 | Guerra et al. |
| 11,229,770 | B2 | 1/2022 | Chou et al. |
| 11,234,723 | B2 | 2/2022 | Ogle |
| 11,253,277 | B2 | 2/2022 | Buck et al. |
| 11,259,820 | B2 | 3/2022 | Walzman |
| 11,259,821 | B2 | 3/2022 | Buck et al. |
| 11,266,434 | B2 | 3/2022 | MeRae et al. |
| 11,272,945 | B2 | 3/2022 | Shrivastava et al. |
| 2003/0187475 | A1* | 10/2003 | Tsugita .................. A61F 2/013 606/200 |
| 2005/0004594 | A1* | 1/2005 | Nool .................. A61F 2/013 604/528 |
| 2005/0159716 | A1* | 7/2005 | Kobayashi .................. A61M 1/82 604/317 |
| 2005/0228423 | A1 | 10/2005 | Khashayar et al. |
| 2007/0075161 | A1 | 4/2007 | Ivri |
| 2007/0129679 | A1 | 6/2007 | Bonnette et al. |
| 2007/0135779 | A1 | 6/2007 | Lalomia et al. |
| 2007/0239182 | A1* | 10/2007 | Glines .................. A61B 17/320758 606/159 |
| 2008/0103433 | A1 | 5/2008 | Nazarifar et al. |
| 2008/0147023 | A1 | 6/2008 | Hopkins et al. |
| 2010/0185150 | A1* | 7/2010 | Zacharias .................. A61M 1/74 604/119 |
| 2010/0191169 | A1 | 7/2010 | Chang |
| 2010/0191170 | A1 | 7/2010 | Chang |
| 2010/0204672 | A1* | 8/2010 | Lockhart .................. A61B 17/22 604/523 |
| 2011/0166496 | A1 | 7/2011 | Criado et al. |
| 2012/0041360 | A1 | 2/2012 | Gerg et al. |
| 2012/0059340 | A1* | 3/2012 | Larsson .................. A61M 1/743 604/319 |
| 2013/0150782 | A1* | 6/2013 | Sorensen .................. A61M 1/742 604/319 |
| 2013/0267919 | A1* | 10/2013 | Caso .................. A61M 1/74 604/319 |
| 2014/0271273 | A1 | 9/2014 | Carpenter |
| 2014/0323906 | A1 | 10/2014 | Peatfield et al. |
| 2015/0283309 | A1* | 10/2015 | Look .................. A61M 1/84 606/127 |
| 2015/0327875 | A1 | 11/2015 | Look et al. |
| 2016/0089227 | A1 | 3/2016 | Loh |
| 2016/0128869 | A1 | 5/2016 | Zacharias |
| 2016/0367272 | A1 | 12/2016 | Garrison et al. |
| 2017/0043066 | A1 | 2/2017 | Laub |
| 2017/0100142 | A1 | 4/2017 | Look et al. |
| 2017/0181760 | A1* | 6/2017 | Look .................. A61M 1/84 |
| 2017/0368309 | A1 | 12/2017 | Garrison et al. |
| 2018/0028359 | A1 | 2/2018 | Gordon et al. |
| 2018/0049920 | A1 | 2/2018 | Charles |
| 2018/0207397 | A1* | 7/2018 | Look .................. A61M 25/0029 |
| 2018/0256177 | A1 | 9/2018 | Cooper et al. |
| 2018/0353194 | A1 | 12/2018 | Shaffer et al. |
| 2019/0108540 | A1 | 4/2019 | Look et al. |
| 2019/0125512 | A1 | 5/2019 | Macdonald et al. |
| 2019/0133616 | A1 | 5/2019 | Sachar et al. |
| 2019/0133617 | A1 | 5/2019 | Look et al. |
| 2019/0142567 | A1 | 5/2019 | Janardhan et al. |
| 2019/0142568 | A1 | 5/2019 | Janardhan et al. |
| 2019/0167287 | A1 | 6/2019 | Vale et al. |
| 2019/0167406 | A1 | 6/2019 | Janardhan et al. |
| 2019/0209745 | A1 | 7/2019 | Hanson et al. |
| 2019/0216476 | A1 | 7/2019 | Bose et al. |

(56) References Cited

U.S. PATENT DOCUMENTS

| | | |
|---|---|---|
| 2019/0239910 A1 | 8/2019 | Brady et al. |
| 2019/0262120 A1 | 8/2019 | Walzman |
| 2019/0274704 A1 | 9/2019 | Jenson et al. |
| 2019/0307947 A1 | 10/2019 | Stubkjaer et al. |
| 2019/0328410 A1 | 10/2019 | Look et al. |
| 2019/0350604 A1 | 11/2019 | Slee et al. |
| 2019/0351182 A1 | 11/2019 | Chou et al. |
| 2019/0366042 A1 | 12/2019 | Garrison et al. |
| 2019/0374128 A1 | 12/2019 | Palushi et al. |
| 2019/0381223 A1* | 12/2019 | Culbert ............... A61M 1/804 |
| 2019/0381303 A1 | 12/2019 | Angel et al. |
| 2019/0388109 A1* | 12/2019 | Cai ............... A61B 17/22004 |
| 2020/0015826 A1 | 1/2020 | Chang |
| 2020/0015840 A1 | 1/2020 | Mallaby |
| 2020/0016369 A1 | 1/2020 | Garrison et al. |
| 2020/0022711 A1 | 1/2020 | Look et al. |
| 2020/0022712 A1 | 1/2020 | Deville et al. |
| 2020/0023160 A1 | 1/2020 | Chou et al. |
| 2020/0023164 A1 | 1/2020 | Tran et al. |
| 2020/0029998 A1 | 1/2020 | Ogle et al. |
| 2020/0038576 A1 | 2/2020 | Garrison et al. |
| 2020/0046368 A1 | 2/2020 | Merritt et al. |
| 2020/0046389 A1 | 2/2020 | Galdonik et al. |
| 2020/0046939 A1 | 2/2020 | Garrison et al. |
| 2020/0046940 A1 | 2/2020 | Garrison et al. |
| 2020/0078029 A1 | 3/2020 | Hansen et al. |
| 2020/0086083 A1 | 3/2020 | Porter et al. |
| 2020/0093503 A1 | 3/2020 | Deville et al. |
| 2020/0121336 A1 | 4/2020 | Tsukamoto et al. |
| 2020/0121356 A1 | 4/2020 | Look et al. |
| 2020/0155178 A1 | 5/2020 | Culbert et al. |
| 2020/0164178 A1 | 5/2020 | Garrison et al. |
| 2020/0170666 A1 | 6/2020 | Trosper et al. |
| 2020/0179576 A1 | 6/2020 | Wood |
| 2020/0179578 A1 | 6/2020 | Look et al. |
| 2020/0187965 A1 | 6/2020 | Garrison et al. |
| 2020/0187979 A1 | 6/2020 | Bowman |
| 2020/0205840 A1 | 7/2020 | Adawi et al. |
| 2020/0206457 A1 | 7/2020 | Boling |
| 2020/0206458 A1 | 7/2020 | Mullins et al. |
| 2020/0214726 A1 | 7/2020 | Anand et al. |
| 2020/0215306 A1 | 7/2020 | Garrison et al. |
| 2020/0246014 A1 | 8/2020 | Walzman |
| 2020/0253624 A1 | 8/2020 | Gamba et al. |
| 2020/0276411 A1 | 9/2020 | Ogle et al. |
| 2020/0281610 A1 | 9/2020 | Look et al. |
| 2020/0281611 A1 | 9/2020 | Kelly et al. |
| 2020/0289136 A1 | 9/2020 | Chou |
| 2020/0289722 A1 | 9/2020 | Culbert et al. |
| 2020/0297362 A1 | 9/2020 | DeVille et al. |
| 2020/0297363 A1 | 9/2020 | Look et al. |
| 2020/0297365 A1 | 9/2020 | Bowman et al. |
| 2020/0297410 A1 | 9/2020 | Nguyen et al. |
| 2020/0297912 A1 | 9/2020 | Criado et al. |
| 2020/0315642 A1 | 10/2020 | Greenhalgh et al. |
| 2020/0316348 A1 | 10/2020 | Ascher et al. |
| 2020/0324079 A1 | 10/2020 | Jalgaonkar et al. |
| 2020/0337716 A1 | 10/2020 | Garrison et al. |
| 2020/0345904 A1 | 11/2020 | Casey et al. |
| 2020/0345981 A1 | 11/2020 | Garrison et al. |
| 2020/0352583 A1 | 11/2020 | Goyal et al. |
| 2020/0367917 A1 | 11/2020 | Teigen et al. |
| 2020/0375616 A1 | 12/2020 | Fitz et al. |
| 2020/0376175 A1* | 12/2020 | Hartwell ............... A61M 1/90 |
| 2020/0383698 A1 | 12/2020 | Miao et al. |
| 2020/0397446 A1 | 12/2020 | Chang |
| 2020/0397451 A1 | 12/2020 | Feltyberger et al. |
| 2020/0397452 A1 | 12/2020 | Twomey et al. |
| 2020/0397465 A1 | 12/2020 | Nakano et al. |
| 2020/0397957 A1 | 12/2020 | Teigen et al. |
| 2021/0022843 A1 | 1/2021 | Hauser |
| 2021/0038236 A1 | 2/2021 | Ma |
| 2021/0038779 A1 | 2/2021 | Lorenzo |
| 2021/0045758 A1 | 2/2021 | Garrison et al. |
| 2021/0045760 A1 | 2/2021 | Ulm, III |
| 2021/0052296 A1 | 2/2021 | Garrison |
| 2021/0068861 A1 | 3/2021 | Bonnette et al. |
| 2021/0069467 A1 | 3/2021 | Garrison et al. |
| 2021/0069468 A1 | 3/2021 | Keating et al. |
| 2021/0077116 A1 | 3/2021 | Ferrera et al. |
| 2021/0077134 A1 | 3/2021 | Vale et al. |
| 2021/0085348 A1 | 3/2021 | Nguyen |
| 2021/0085931 A1 | 3/2021 | Green et al. |
| 2021/0093344 A1 | 4/2021 | Janardhan et al. |
| 2021/0100974 A1 | 4/2021 | Walzman |
| 2021/0100987 A1 | 4/2021 | Sehultz et al. |
| 2021/0110419 A1 | 4/2021 | Look et al. |
| 2021/0113224 A1 | 4/2021 | Dinh |
| 2021/0121281 A1 | 4/2021 | Walzman |
| 2021/0128182 A1 | 5/2021 | Teigen et al. |
| 2021/0128893 A1 | 5/2021 | Twomey et al. |
| 2021/0138193 A1 | 5/2021 | Garrison et al. |
| 2021/0138194 A1 | 5/2021 | Garrison et al. |
| 2021/0153883 A1 | 5/2021 | Casey et al. |
| 2021/0161544 A1 | 6/2021 | Casey |
| 2021/0161639 A1 | 6/2021 | Walzman |
| 2021/0169509 A1 | 6/2021 | Goyal |
| 2021/0170148 A1 | 6/2021 | Green et al. |
| 2021/0186534 A1 | 6/2021 | Hunt et al. |
| 2021/0219998 A1 | 7/2021 | Thomas |
| 2021/0220109 A1 | 7/2021 | Walzman |
| 2021/0220528 A1 | 7/2021 | Jalgaonkar et al. |
| 2021/0228222 A1* | 7/2021 | Porter ............... A61M 1/74 |
| 2021/0228844 A1 | 7/2021 | Ogle |
| 2021/0228847 A1 | 7/2021 | Kume et al. |
| 2021/0236148 A1 | 8/2021 | Marchand et al. |
| 2021/0236150 A1 | 8/2021 | Arad Hadar |
| 2021/0236257 A1 | 8/2021 | Walzman |
| 2021/0259719 A1 | 8/2021 | Griffin |
| 2021/0267745 A1 | 9/2021 | Walzman |
| 2021/0275197 A1 | 9/2021 | Vale et al. |
| 2021/0298773 A1 | 9/2021 | Echarri et al. |
| 2021/0298775 A1 | 9/2021 | Nguyen et al. |
| 2021/0299343 A1 | 9/2021 | Criado et al. |
| 2021/0322051 A1 | 10/2021 | Hatta et al. |
| 2021/0322053 A1 | 10/2021 | Kobayashi et al. |
| 2021/0322738 A1 | 10/2021 | Kume et al. |
| 2021/0330332 A1 | 10/2021 | Chou et al. |
| 2021/0338255 A1 | 11/2021 | Alesi et al. |
| 2021/0346040 A1 | 11/2021 | Panian |
| 2021/0353314 A1* | 11/2021 | Porter ............... A61M 1/75 |
| 2021/0353316 A1 | 11/2021 | Wallace et al. |
| 2021/0353323 A1 | 11/2021 | Teigen et al. |
| 2021/0361305 A1 | 11/2021 | Mogi et al. |
| 2021/0378691 A1 | 12/2021 | Panian |
| 2021/0378696 A1 | 12/2021 | Yang et al. |
| 2021/0393280 A1 | 12/2021 | Cortinas Villazon et al. |
| 2022/0000500 A1 | 1/2022 | Arad Hadar et al. |
| 2022/0000502 A1 | 1/2022 | Ulm, III et al. |
| 2022/0000505 A1 | 1/2022 | Hauser |
| 2022/0000506 A1 | 1/2022 | Hauser |
| 2022/0000507 A1 | 1/2022 | Hauser |
| 2022/0008090 A1 | 1/2022 | Look et al. |
| 2022/0015798 A1 | 1/2022 | Marchand et al. |
| 2022/0022898 A1 | 1/2022 | Cox et al. |
| 2022/0022899 A1 | 1/2022 | Girdhar et al. |
| 2022/0022900 A1 | 1/2022 | Nguyen et al. |
| 2022/0031931 A1 | 2/2022 | Stout |
| 2022/0054150 A1 | 2/2022 | Dholakia et al. |
| 2022/0054151 A1 | 2/2022 | Shiffette |
| 2022/0054153 A1 | 2/2022 | Albers et al. |
| 2022/0061870 A1 | 3/2022 | Mintz |
| 2022/0061871 A1 | 3/2022 | Mintz |
| 2022/0061872 A1 | 3/2022 | Mintz |
| 2022/0062588 A1 | 3/2022 | Mintz |
| 2022/0087696 A1 | 3/2022 | Maini et al. |
| 2022/0168000 A1* | 6/2022 | Naglreiter ............... A61B 17/22 |

FOREIGN PATENT DOCUMENTS

| | | |
|---|---|---|
| WO | 20140151209 | 9/2014 |
| WO | 2017062927 A1 | 4/2017 |
| WO | 2018019829 | 2/2018 |
| WO | 2020023541 | 1/2020 |

(56) References Cited

FOREIGN PATENT DOCUMENTS

| | | |
|---|---|---|
| WO | 20200145928 | 7/2020 |
| WO | 20200167276 | 8/2020 |
| WO | 2021012058 | 1/2021 |
| WO | 2021016213 | 1/2021 |
| WO | 2021073572 | 4/2021 |
| WO | 2021083832 | 5/2021 |
| WO | 2021113962 | 6/2021 |
| WO | 2021113970 | 6/2021 |
| WO | 2021123395 | 6/2021 |
| WO | 2021151969 | 8/2021 |
| WO | 2021178696 | 9/2021 |
| WO | 2021242963 | 12/2021 |
| WO | 20210250133 | 12/2021 |
| WO | 2022020366 | 1/2022 |
| WO | 2022040615 | 2/2022 |

OTHER PUBLICATIONS

International Search Report and Written Opinion issued for Application No. PCT/US2022/025918, dated Jun. 29, 2022.
Office Action issued for U.S. Appl. No. 17/726,787, dated Dec. 1, 2022.
Office Action issued for U.S. Appl. No. 17/726,788, dated Nov. 30, 2022.

* cited by examiner

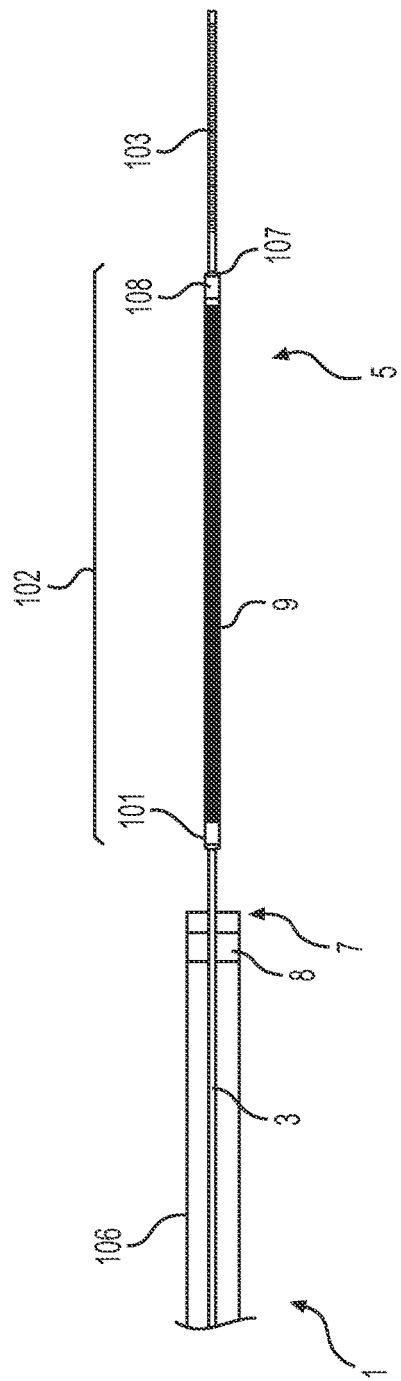
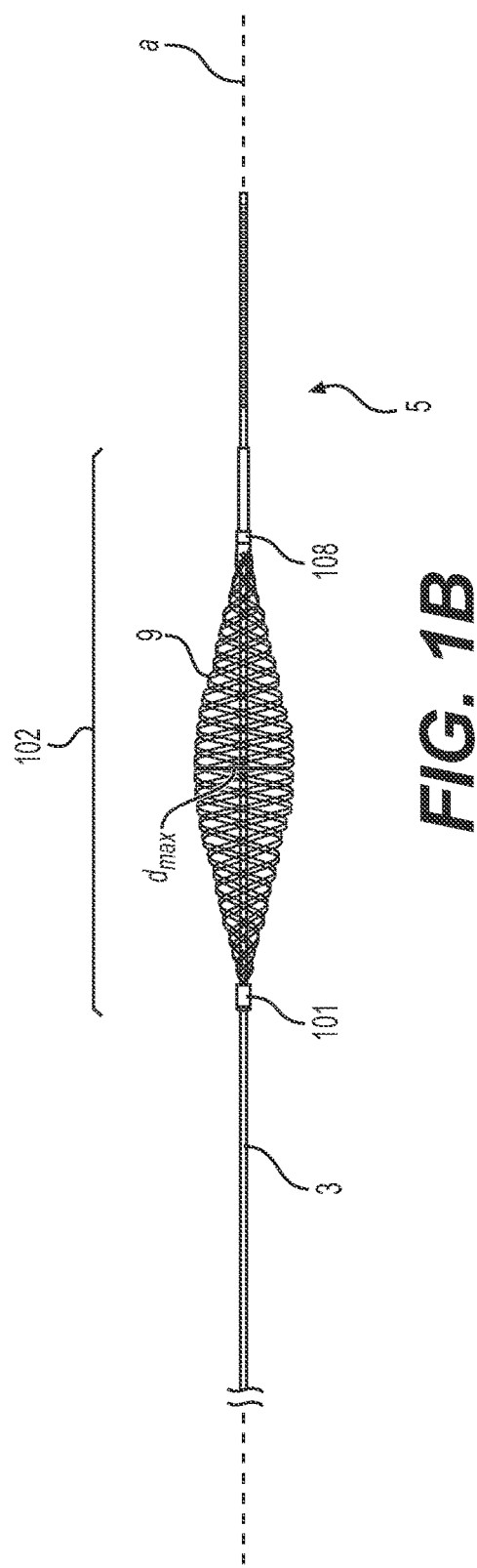

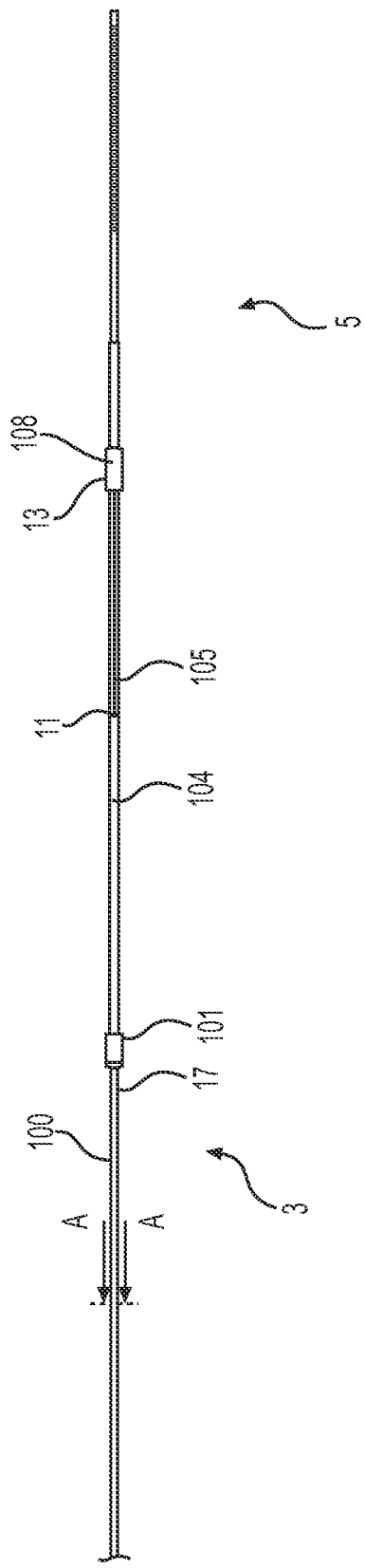
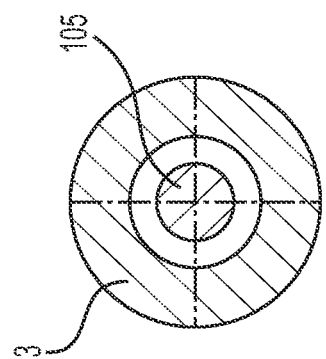
FIG. 1C
FIG. 1D

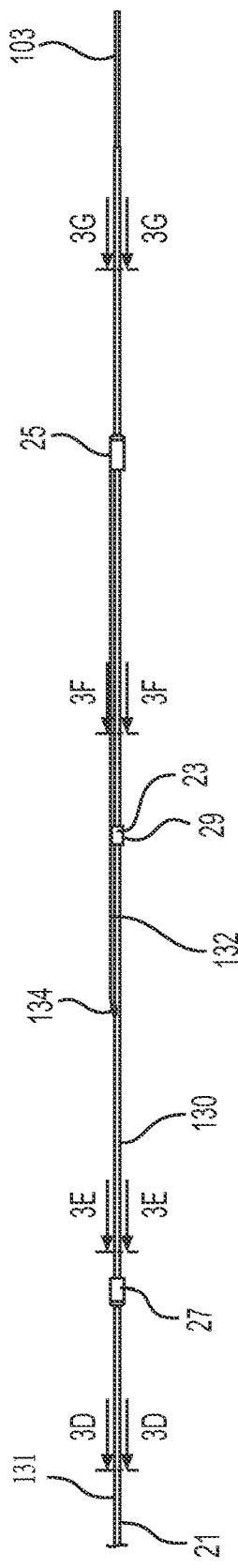
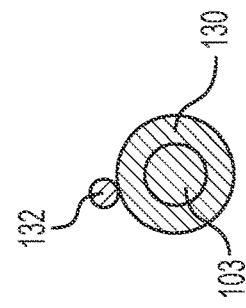
FIG. 3C
FIG. 3D  FIG. 3E  FIG. 3F  FIG. 3G

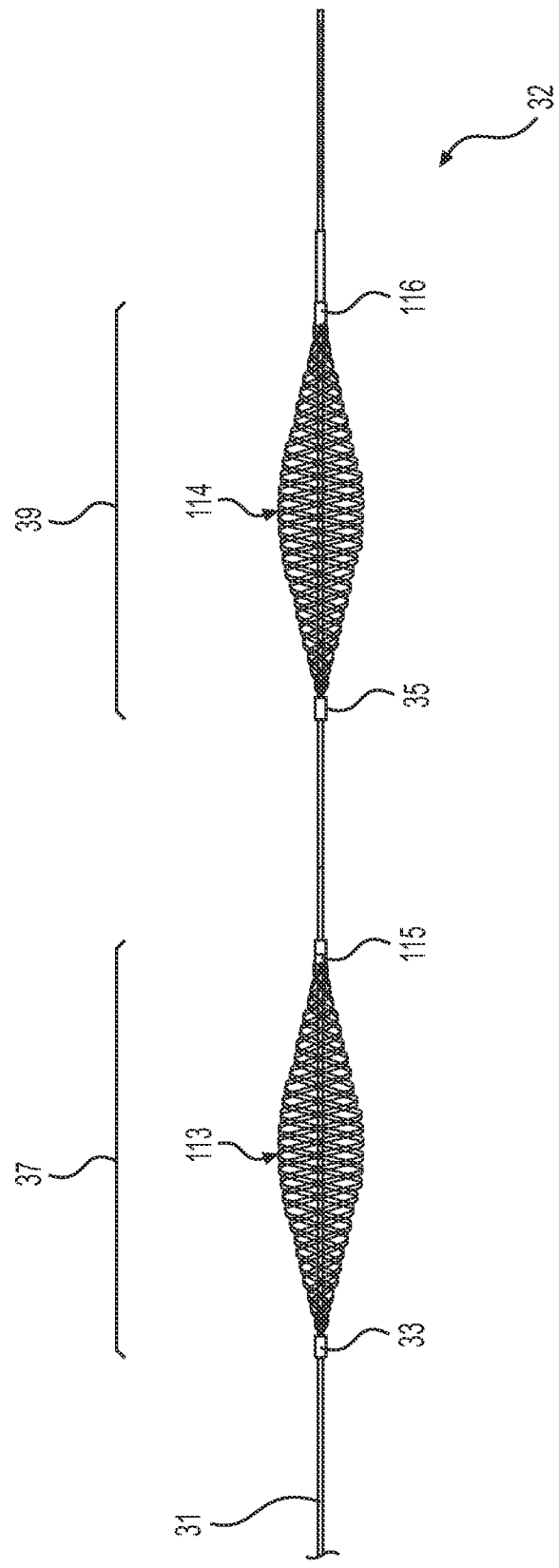

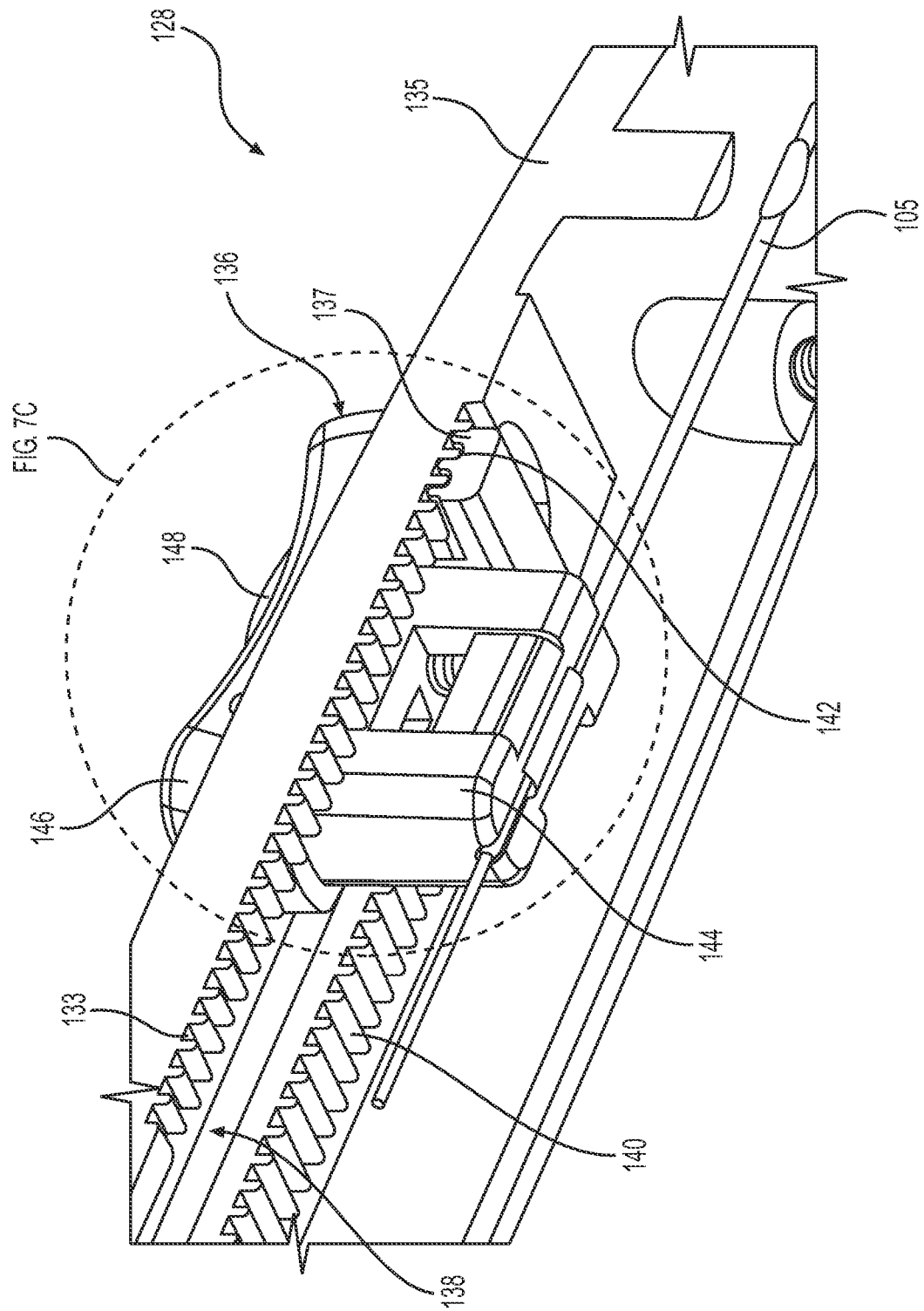

THROMBUS ASPIRATION SYSTEM AND METHODS FOR CONTROLLING BLOOD LOSS

CROSS-REFERENCE TO RELATED APPLICATIONS

This application claims the benefit of U.S. Provisional Application 63/180,291, filed Apr. 27, 2021, which is incorporated by reference herein in its entirety for all purposes.

FIELD

This invention relates to medical devices for thrombus removal, and more particularly to thrombus aspiration systems.

BACKGROUND

It is often desirable to remove tissue from the body in a minimally invasive manner as possible, so as not to damage other tissues. For example, removal of tissue (e.g., blood clots) from the vasculature may improve patient conditions and quality of life.

Many vascular system problems stem from insufficient blood flow through blood vessels. One causes of insufficient or irregular blood flow is a blockage within a blood vessel referred to as a blood clot, or thrombus. Thrombi can occur for many reasons, including after a trauma such as surgery, or due to other causes. For example, a large percentage of the more than 1.2 million heart attacks in the United States are caused by blood clots (thrombi) which form within a coronary artery.

When a thrombus forms, it may effectively stop the flow of blood through the zone of formation. If the thrombus extends across the interior diameter of an artery, it may cut off the flow of blood through the artery. If one of the coronary arteries is 100% thrombosed, the flow of blood is stopped in that artery, resulting in a shortage of oxygen carrying red blood cells, e.g., to supply the muscle (myocardium) of the heart wall. Such a thrombosis is unnecessary to prevent loss of blood but can be undesirably triggered within an artery by damage to the arterial wall from atherosclerotic disease. Thus, the underlying disease of atherosclerosis may not cause acute oxygen deficiency (ischemia) but can trigger acute ischemia via induced thrombosis. Similarly, thrombosis of one of the carotid arteries can lead to stroke because of insufficient oxygen supply to vital nerve centers in the cranium. Oxygen deficiency reduces or prohibits muscular activity, can cause chest pain (angina pectoris), and can lead to death of myocardium which permanently disables the heart to some extent. If the myocardial cell death is extensive, the heart will be unable to pump sufficient blood to supply the body's life sustaining needs. The extent of ischemia is affected by many factors, including the existence of collateral blood vessels and flow which can provide the necessary oxygen.

Clinical data indicates that clot removal may be beneficial or even necessary to improve outcomes. For example, in the peripheral vasculature, inventions and procedures can reduce the need for an amputation by 80 percent. The ultimate goal of any modality to treat these conditions of the arterial or venous system is to remove the blockage or restore patency, quickly, safely, and cost effectively. This may be achieved by thrombus dissolution, fragmentation, thrombus aspiration or a combination of these methods.

Catheter directed thrombectomy and thrombolysis are commonly perceived to be less traumatic, less likely to decrease the morbidity and mortality associated with conventional surgical techniques. In recent years, direct administration of chemical lysing agents into the coronary arteries has shown to be of some benefit to patients who have thrombosed coronary arteries. In this procedure, a catheter is placed immediately in front of the blockage and a drip of streptokinase is positioned to be directed at the upstream side of the thrombus. Streptokinase is an enzyme which is able in time to dissolve the fibrin molecule. This procedure can take several hours and is not always successful in breaking up the thrombus. Furthermore, it can lead to downstream thrombus fragments (emboli) which can lead to blockage of small diameter branches.

Thrombectomy is a technique for mechanical removal of blood clots in an artery or vein. It refers to physically removing a clot as opposed to employing chemical lysis to dissolve it. Multiple devices have been introduced to break up and remove clot and plaque, but each has its own shortcomings. Specifically, the existing systems do not provide adequate methods for breaking up the clot into smaller pieces for subsequent aspiration. Also, they do not provide a method for removing the thrombectomy device over a guidewire and reinserting into the same location to complete the procedure. Furthermore, conventional aspiration systems offer little control over the amount of blood lost during the procedure. There is a need for improved thrombectomy devices and aspiration systems that are safer and more effective for removing thrombus and plaque from the vascular system.

SUMMARY

Aspiration systems and methods are disclosed herein for controlling blood loss during thrombus removal. The aspiration systems include, at least, an aspiration catheter, a thrombus retrieval device extending through the aspiration catheter, and an aspiration tubing fluidically coupled to the aspiration catheter. An aspiration lumen extends through the aspiration catheter and the aspiration tubing. A sensor measures a flow parameter associated with a liquid within the aspiration lumen. The aspiration systems further include a receptacle configured to collect liquid aspirated by the aspiration catheter. A vacuum line is fluidically coupled to the receptacle, and a regulator adjusts the vacuum pressure within the vacuum line. A vacuum controller is operably coupled to the sensor and the regulator. The vacuum controller is configured to receive the flow parameter from the sensor, compare the flow parameter to a target range for the flow parameter, and send an automatic control signal to the regulator based on a comparison of the flow parameter to the target range. The automatic control signal causes the regulator to adjust the vacuum pressure within the vacuum line.

In some implementations, the automatic control signal causes the regulator to decrease the vacuum pressure upon a determination that the flow parameter is above an upper limit of the target range, and to increase the vacuum pressure upon a determination that the flow parameter is below a lower limit of the target range. For example, the upper limit can be a flow rate from 70 mL per minute to 130 mL per minute, and the lower limit can be a flow rate from 0 mL per minute to 40 mL per minute. In some examples, the vacuum controller is configured to adjust the flow rate to an intermediate level, such as, for example, from 20 mL per minute to 50 mL per minute. Increases and decreases in vacuum pressure can occur in a stepwise manner. In some implementations, the vacuum controller can activate an aspiration program that causes increases and decreases of vacuum pressure in a stepwise manner. In some examples, the aspiration program is activated upon receipt of information from one or more manual inputs in communication with the regulator, the vacuum controller, or both.

The receptacle is fluidically coupled to the aspiration tubing, the aspiration catheter, and the vacuum line. In some implementations, an intake port on the receptacle provides the coupling between the receptacle and the aspiration tubing, and a vacuum port on the receptacle provides the coupling between the receptacle and the vacuum line. The receptacle can include a receptacle vent in communication with the regulator or the vacuum controller. The receptacle vent opens upon receipt of a venting signal from the regulator or vacuum controller.

The aspiration system includes one or more sensors for measuring flow parameters, such as, for example, a flow rate. Some implementations can include a plurality of sensors configured to measure one or more parameters associated with fluid flow at disparate points along a length of the aspiration lumen, and to send the measured parameters to the vacuum controller. The sensor may or may not contact the liquid within the aspiration lumen.

Some implementations can further include an air leak sensor in communication with the vacuum controller or the regulator. The air leak sensor can detect air flow through the aspiration tubing and send a leak signal to the vacuum controller, the regulator, or the vacuum pump upon detection of air through the aspiration tubing. The vacuum controller, regulator, or pump can slow or stop the vacuum flow while the air leak is addressed. In some implementations, the vacuum controller is configured to delay detection of air leaks during a vacuum initialization period. Alternatively, or in addition, the vacuum controller can be configured to delay controlling the vacuum in response to detection of air leaks during a vacuum initialization period.

In some implementations of the system, the regulator adjusts the vacuum pressure within the vacuum line by manipulating a valve that opens the vacuum line to the atmosphere. In some implementations, the regulator adjusts the vacuum pressure within the vacuum line by manipulating a valve that alters the flow capacity of the vacuum line. The vacuum line can have a disposable portion and a reusable portion. The disposable portion can be coupled to the reusable portion at a connector. Some implementations of the system include a vacuum pump. Some implementations can include a power sensor configured to synchronize the delivery of power between the pump and the vacuum controller.

The vacuum controller sends signals to one or more components of the system to regulate flow of air in the vacuum line and blood through the aspiration lumen. The vacuum controller can be, in some examples, a microprocessor controller. It can include an analog to digital converter and a digital to analog converter. In some examples, the vacuum controller is configured to measure a frequency from the flow parameter. The vacuum controller can operate independently. For example, the vacuum controller is capable of operating without input from external sources such as a computer.

Some implementations of the systems include one or more manual inputs in communication with the vacuum controller, the regulator, and/or a receptacle vent. The manual input is configured to accept a manual command and send a first manual control signal responsive to the manual command to one or more of the vacuum controller, the regulator, and/or the receptacle vent. In some examples, upon receipt of the first manual control signal, the vacuum controller stops one or more steps of comparing the flow parameter to a target range for the flow parameter, forming an automatic control signal, and/or sending the automatic control signal to the regulator. In some implementations, the vacuum controller is configured to send a second manual control signal to the regulator and/or receptacle vent based on the first manual control signal. The regulator controls the vacuum pressure within the vacuum line upon receipt of the first manual control signal and/or the second manual control signal. The receptacle vent opens or shuts upon receipt of the first manual control signal and/or the second manual control signal. Some systems can also include an indicator in communication with the flow sensor. The indicator is configured to inform a user of a characteristic of the flow parameter.

In some implementations, at least one braided assembly extends over a distal region of the thrombus retrieval device. The braided assembly can include a braid having a shape memory of a collapsed configuration.

In some implementations, the aspiration system further comprises a clamp coupled to the aspiration tubing and a switch operably coupled to the clamp, the switch comprising a closed configuration and an open configuration, wherein the switch in the closed configuration causes the clamp to stop fluid flow through the aspiration tubing, and wherein the switch in the open configuration causes the clamp to allow fluid flow through the aspiration tubing. The switch can be in communication with the vacuum controller and/or the regulator. Shifting the switch to the open configuration can send a surge protection signal to the regulator and/or to the vacuum controller. The regulator and/or the vacuum controller can reduce the vacuum pressure upon receipt of the surge protection signal.

Methods of controlling blood loss during thrombus removal are disclosed herein. The methods include positioning an aspiration catheter within the vascular system of a subject and positioning a thrombus retrieval device within the vascular system of the subject through the aspiration catheter. The aspiration catheter is fluidically connected to an aspiration tubing and a vacuum pump. Activation of the vacuum pump initiates the flow of blood through the aspiration catheter and the aspiration tubing. A sensor measures a flow parameter of the blood within the aspiration tubing. The flow parameter from the sensor is received at a vacuum controller. The flow parameter is compared to a target range for the flow parameter, and an automatic control signal is sent to the regulator based on a comparison of the flow parameter to the target range. The vacuum pressure within the vacuum line is adjusted according to information stored in the automatic control signal.

In some implementations, the vacuum pump is activated at full power, and adjustments to the vacuum pressure are regulated by the vacuum controller while the vacuum pump runs at full power.

The step of adjusting the vacuum pressure can include decreasing the vacuum pressure upon a determination that the flow parameter is above an upper limit of the target range (for example, an upper limit of a flow rate from 70 mL per minute to 130 mL per minute). The step of decreasing the vacuum pressure can include lowering the vacuum pressure in a stepwise manner. In some implementations, the vacuum pressure is decreased until the measured flow parameter reaches an intermediate level flow rate of 20 mL per minute to 50 mL per minute. Some methods include a step of activating an aspiration program upon receipt of a manual command from one or more manual inputs in communication with the regulator and/or the vacuum controller, and the aspiration program includes lowering the vacuum pressure in a stepwise manner.

The step of adjusting the vacuum pressure can include increasing the vacuum pressure upon a determination that the flow parameter is below a lower limit of the target range (for example, a lower limit of a flow rate of from 0 mL per minute to 50 mL per minute). the step of increasing the vacuum pressure can include raising the vacuum pressure in a stepwise manner. In some implementations, the vacuum pressure is raised until the measured flow parameter reaches an intermediate level flow rate of 20 mL per minute to 50 mL per minute. Some methods include a step of activating an aspiration program upon receipt of a manual command from one or more manual inputs in communication with the regulator and/or the vacuum controller, and the aspiration program includes raising the vacuum pressure in a stepwise manner.

In some implementations, the step of adjusting the vacuum pressure within the vacuum line comprises manipulating a valve that opens the vacuum line to the atmosphere. In some implementations, the step of adjusting the vacuum pressure within the vacuum line alters the flow capacity of the vacuum line.

The step of measuring a flow parameter can include measuring a flow rate. Some method implementations use a plurality of sensors to measure one or more flow parameters of the blood at disparate points along the length of the aspiration lumen. The one or more flow parameters are received at the vacuum controller. The methods can further include a step of measuring a frequency from the flow parameter at the vacuum controller.

Some method implementations can include a step of detecting air within the aspiration tubing and sending a leak signal to the regulator, the pump, or to the vacuum controller. In some implementations, the step of detecting air within the aspiration tubing or the step of sending a leak signal to the regulator or the pump is delayed during initialization of the vacuum.

Some method implementations can include a step of accepting a manual command at a manual input and sending a first manual control signal responsive to the manual command to one or more of the vacuum controller, the regulator, or a receptacle vent. Upon receipt of the first manual control signal, the vacuum controller can stops sending automatic control signals to the regulator. In some implementations, a second manual control signal is formed at the vacuum controller (based on the first manual control signal) and the second manual control signal is sent to the regulator and/or receptacle vent. Some method implementations can include a step of receiving the first manual control signal or the second manual control signal at the regulator and controlling vacuum pressure within the vacuum line based on the first manual control signal or the second manual control signal. Some method implementations can include a step of receiving the first manual control signal or the second manual control signal at the receptacle vent and opening or shutting the vent based on the first manual control signal or the second manual control signal.

Some method implementations can include a step of receiving information from the flow sensor at an indicator and informing a user of a characteristic of the flow parameter using the indicator.

Some method implementations can include a step of shifting a switch from a closed configuration to an open configuration, wherein shifting the switch to the open configuration causes a clamp coupled to the aspiration tubing to allow fluid flow through the aspiration tubing. A surge protection signal can be sent upon shifting of the switch to the open configuration and received at the controller or regulator. The vacuum pressure can be decreased upon receipt of the surge protection signal.

Some method implementations can include a step of synchronizing the delivery of power between the vacuum pump and the vacuum controller.

DESCRIPTION OF DRAWINGS

The device is explained in even greater detail in the following drawings. The drawings are merely exemplary and certain features may be used singularly or in combination with other features. The drawings are not necessarily drawn to scale.

FIG. 1A is a side section view of an implementation of the thrombectomy device having a single braided assembly in the collapsed configuration.

FIG. 1B is a side view showing the distal region of the thrombectomy device carrying the braided assembly of FIG. 1A. The braided assembly is shown in an expanded configuration.

FIG. 1C is a side view showing the distal region of the thrombectomy device of FIG. 1A. The braided assembly is not included in this view.

FIG. 1D is a cross sectional view of the implementation of FIG. 1A, taken along lines A-A of FIG. 1C.

FIG. 3C is a side view of the distal region of the thrombectomy device of FIG. 3A. The braided assembly is not included in this view.

FIG. 3D shows a cross sectional view taken along line 3D-3D of FIG. 3C.

FIG. 3E shows a cross sectional view taken along line 3E-3E of FIG. 3C.

FIG. 3F shows a cross sectional view taken along line 3F-3F of FIG. 3C.

FIG. 3G shows a cross sectional view taken along line 3G-3G of FIG. 3C.

FIG. 4 shows an additional implementation of the thrombectomy device having multiple expandable braided assemblies.

FIG. 7B shows a bottom up, inside view of the locking slider of the handle implementation of FIG. 7A.c

DETAILED DESCRIPTION

Figure 2:
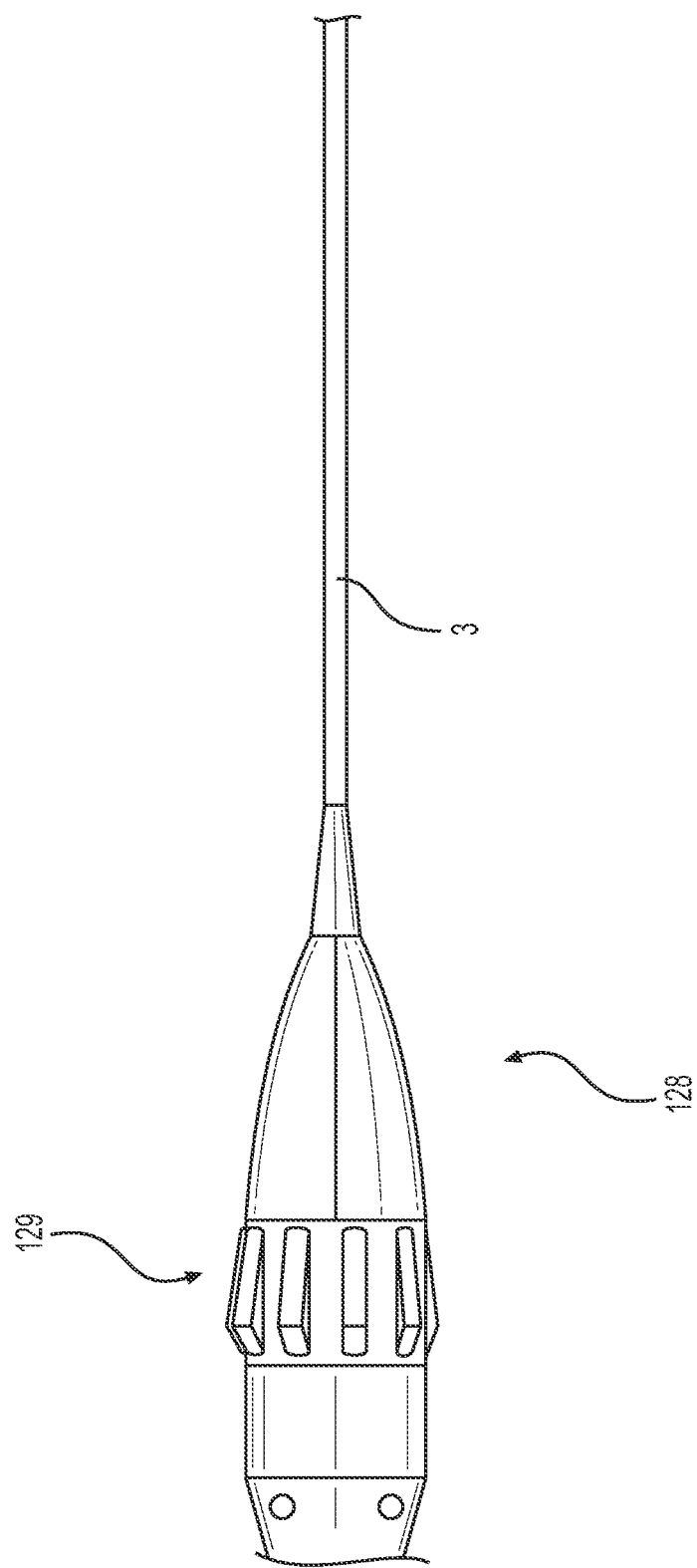
FIG. 2 shows a side view of an implementation of a handle that can be used to control expansion and retraction of a braided assembly.

The systems and methods disclosed herein aim to reduce the amount of blood lost during procedures that utilize aspiration to remove thrombus from the vasculature. The systems include a vacuum controller for an aspiration pump that is used in conjunction with an aspiration catheter and an aspiration tubing. The aspiration tubing is equipped with a flow sensor in communication with the vacuum controller. The vacuum controller monitors the flow rate of blood being aspirated by the pump and communicates with a vacuum regulator to raise the vacuum if the flow rate gets to low (for example, when obstructed by a clot). The vacuum controller also communicates with the vacuum regulator to lower the vacuum if the flow rate gets too high. This lowering of the vacuum is a safety feature designed to prevent the system from aspirating blood instead of clot. Applying only the vacuum needed to remove the clot prevents unnecessary blood loss. Furthermore, damage to the vasculature is reduced because the amount of time the system applies full vacuum is minimized. The system can increase or decrease pressure gradually, or in a stepwise manner, to ensure the practitioner has sufficient time to respond to sudden changes in flow rate. The system can also include a variety of manual inputs to slow, pause, or stop the automated flow control processes.

The system disclosed herein integrates flow and vacuum control, using flow rate to inform the desired vacuum level. Conventional systems do not offer this feature. Many prioritize improving aspiration efficiency over controlling blood loss. Furthermore, conventional systems often adjust vacuum level based on pressure sensors within the aspiration tubing. Because the disclosed system responds specifically to the parameter of interest—the amount of blood flowing through the catheter—it responds more accurately than pressure measurement-based systems. With this system, the user can tune the flow rate, defining minimum and maximum allowed flow rates, and then automate control of the vacuum and flow rate according to those thresholds. This automation reduces the need for the practitioner to monitor and adjust the procedure for blood loss (though the practitioner is able to override the automation when necessary, via the aforementioned manual inputs). Advantageously, the system minimizes the necessary procedure time by optimizing the aspiration process.

The aspiration system can be used with a variety of catheters and vacuum pumps without changing the core aspiration system. It can be provided with all of the necessary components, or can be used with components that are provided by the clinician. Furthermore, the vacuum controller, regulator, and pump can be used in the operating theater but fluidically isolated from the patient, negating the need for extensive sterilization. Flow manipulation occurs within the vacuum line instead of the aspiration lumen—a cleaner design than some conventional systems where valves directly manipulate blood flow within the aspiration lumen. In the disclosed aspiration systems, components that do contact blood can be disposable, whereas fluidically isolated components can be reusable.

The thrombectomy devices disclosed herein remove a thrombus using a braided assembly that can be expanded to a diameter of the practitioner's choosing, enabling the practitioner to custom fit the device to the particular vessel and thrombus and during the procedure. Unlike conventional thrombectomy devices, the diameter of the disclosed braided assembly can be changed mid-procedure as needed. For example, the braided assembly can be opened to a wider diameter to apply more outward force against the thrombus should additional grip be needed for its removal. In some implementations, multiple braided assemblies can be used to address longer thrombi. Each braided assembly can be separately expanded, such that the individual assemblies have different diameters during the procedure.

The device disclosed herein is used to the remove a thrombus, clot, or plaque from the veins or arteries of the body. It includes an aspiration catheter and a retrieval device that extends through the lumen of the aspiration catheter. An expandable braided assembly extends over a distal region of the retrieval device, such that when the retrieval device exits the distal end of the aspiration catheter, the braided assembly is positioned outside of the aspiration catheter. An activation wire extends through the lumen of the retrieval device. The distal end of the activation wire exits the retrieval device at an exit point to connect to and control the expansion of a braided assembly. On the proximal end, the activation wire is attached to a tensioning element. Applying tension to the activation wire causes the braided assembly to expand to a diameter of the practitioner's choosing. For example, the practitioner may apply a first level of tension to deploy the braided assembly to a first, partially expanded configuration and then later decide to widen the diameter to the fully expanded configuration by applying a greater level of tension to the activation wire. The expanded braided assembly contacts the thrombus, clot, or plaque and is pulled proximally toward the aspiration catheter to assist in removal. Hereinafter the device and methods will be described as removing (or being configured to remove) a thrombus. However, it will be understood that the device can also be used to remove clots or plaques from the vasculature with no structural (or only slight structural) modifications. Various implementations of the thrombectomy catheter include a retrieval device with multiple braided assemblies, multiple activation wires, multiple braided sections of a single braided assembly, and retrieval devices with multiple lumens to, for example, enable use with a guidewire.

The following description of certain examples of the inventive concepts should not be used to limit the scope of the claims. Other examples, features, aspects, configurations, implementations, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain advantages and novel features of the aspects and configurations of this disclosure are described herein. The described methods, systems, and apparatus should not be construed as limiting in any way. Instead, the present disclosure is directed toward all novel and nonobvious features and aspects of the various disclosed aspects, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Although the operations of exemplary aspects of the disclosed method may be described in a particular, sequential order for convenient presentation, it should be understood that disclosed aspects can encompass an order of operations other than the particular, sequential order disclosed. For example, operations described sequentially may in some cases be rearranged or performed concurrently. Further, descriptions and disclosures provided in association with one particular aspect or implementation are not limited to that aspect or implementation and may be applied to any aspect or implementation disclosed. It will understood that various changes and additional variations may be made and equivalents may be substituted for elements thereof without departing from the scope of the invention or the inventive concept thereof. Certain aspects and features of any given aspect may be translated to other aspects described herein. In addition, many modifications may be made to adapt a particular situation or device to the teachings of the invention without departing from the essential scope thereof. Therefore, it is intended that the invention not be limited to the particular implementations disclosed herein, but that the invention will include all implementations falling within the scope of the appended claims.

Features, integers, characteristics, compounds, chemical moieties, or groups described in conjunction with a particular aspect, configuration, implementation or example of the invention are to be understood to be applicable to any other aspect, configuration, implementation, or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing aspects. The invention extends to any novel one, or any novel combination, of the features disclosed in this specification (including any accompanying claims, abstract, and drawings), or to any novel one, or any novel combination, of the steps of any method or process so disclosed.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. The terms "about" and "approximately" are defined as being "close to" as understood by one of ordinary skill in the art. In one non-limiting aspect the terms are defined to be within 10%. In another non-limiting aspect, the terms are defined to be within 5%. In still another non-limiting aspect, the terms are defined to be within 1%.

"Optional" or "optionally" means that the subsequently described event or circumstance may or may not occur, and that the description includes instances where said event or circumstance occurs and instances where it does not.

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

The terms "proximal" and "distal" as used herein refer to regions of the aspiration tubing or thrombectomy device. "Proximal" means a region closest to the practitioner during a procedure, while "distal" means a region farther from the practitioner during a procedure.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

A vacuum is a pressure that is less than the local atmospheric pressure. As used herein, "vacuum pressure" indicates the relative pressure, i.e., the differential between ambient pressure and the absolute pressure applied by the vacuum. Thus, an increase in relative vacuum pressure is an increase in the difference between ambient pressure and the absolute vacuum pressure, which increases the force applied by the vacuum. Likewise, a decrease in relative vacuum pressure is a decrease in the difference between ambient pressure and the absolute vacuum pressure, which decreases the force applied by the vacuum.

FIGS. 1A-1D show an implementation of the thrombectomy device 1. FIG. 1A shows the aspiration catheter 106, the retrieval device 3, a collapsed braided assembly 102, and a guidewire tip 103. The aspiration catheter 106 is an elongated tube with reinforced construction that allows a vacuum to be applied at the proximal end to pull clot and emboli out of the artery or vein without collapsing. The aspiration catheter 106 can be formed of a polymer material. The aspiration catheter 106 can include an imaging marker 8 (such as a fluorescent or radiopaque marker) for use in imaging the position of the catheter during a procedure. Thrombus retrieval device 3 extends through aspiration catheter 106. The braided assembly 102 extends over a distal region 5 of the retrieval device 3, such that when the retrieval device 3 exits the distal end 7 of the aspiration catheter 106, the braided assembly 102 is positioned outside of the aspiration catheter 106. In the collapsed configuration, braided assembly 102 is sized and configured for insertion through the aspiration catheter 106 and into an artery or vein. Guidewire tip 103 extends distally from the distal end 107 of the retrieval device 3. The guidewire tip 103 can be flexible, shapeable, and steerable.

The braided assembly 102 is moveable from a collapsed to an expanded configuration. An example of a braided assembly 102 in an expanded configuration is shown in FIG. 1B, but the maximum diameter, $d_{max}$, of the expanded braided assembly 102 can be changed to any value over a continuous range, from a fully collapsed diameter, to a partially expanded diameter, to a fully expanded diameter.

The maximum diameter of the braided assembly, $d_{max}$, is the widest point measured perpendicular to a longitudinal axis, a, extending through the center of the braided assembly 102. The braided assembly 102 can be sized and configured to disrupt and capture one or more clots, plaques, and/or thrombi and pull them toward the aspiration catheter 106 where they can be removed. The braided assembly 102 includes a braid 9, a slidable collar 108, and a fixed attachment point 101 where the braid 9 anchors to the retrieval device 3. The braid 9 may be attached directly to the retrieval device 3 at attachment point 101, or the braid 9 may be attached indirectly to the retrieval device 3 at attachment point 101. In some implementations, the fixed attachment point 101 is a fixed collar that extends around the retrieval device 3, and the braid is welded, bonded, or otherwise adhered to the fixed collar. Regardless, at the fixed attachment point 101, the braid 9 does not move longitudinally relative to the retrieval device 3.

The opposite end of braid 9 is welded, bonded, or otherwise adhered to slidable collar 108. In the implementations shown, the slidable collar 108 is slidably connected to the retrieval device 3 by virtue of its annular shape, which extends circumferentially around the retrieval device 3. The slidable collar 108 slides longitudinally along the retrieval device 3 as braid 9 is expanded and collapsed. The slidable collar 108 can be positioned distally to the fixed attachment point 101 (a distal position), as shown in FIGS. 1A-1C, or the slidable collar 108 can be positioned proximally to the fixed attachment point 101 (a proximal position). In some implementations, slidable collar 108 or fixed attachment point 101 can include a marker that can be viewed using imaging modalities during a procedure. For example, the slidable collar 108 or fixed attachment point 101 can include a fluorescent or radiopaque label.

The braid 9 is composed of multiple strands of wire. The braid 9 takes an elliptical or a spindle shape when expanded, having a maximum diameter $d_{max}$ at or near the center of the braid 9 and narrowing as the braid approaches the fixed attachment point 101 and the slidable collar 108. The wires are formed of a shape memory material such as, but not limited to, shape memory polymers or shape memory metals (e.g., nitinol). The braid 9 has a baseline shape memory of the collapsed configuration, which forms a cylindrical structure around the retrieval device 3, as shown in FIG. 1A. In the activated, expanded configuration, the braid 9 has a tendency to relax toward the collapsed configuration.

When the practitioner is pulling a thrombus or plaque proximally toward aspiration catheter 106 using braided assembly 102, the braid 9 encounters distally oriented drag forces that are strongest along the widest portions (for example, the central region of the braid adjacent $d_{max}$) These drag forces resist the proximally oriented pulling force exerted by the practitioner. The distal end of braid 9 at slidable collar 108 will encounter less drag force while being pulled proximally because the radial force it exerts on the radially adjacent vasculature or thrombus is small, negligible, or non-existent. If the braid is not properly designed, the sliding collar 108 and distal end of the braid 9 will invert into the wider, central regions of the braid 9. Inversion during the procedure can be prevented by optimizing factors such as the pic count (crosses per inch), the wire diameter, the number of wires, and the ply of the braid (sets of overlapping braids). Higher pic counts increase flexibility, while lower pic counts increase longitudinal stiffness. Likewise, a braid with more than one ply (multiple sets of braids nested within each other), will be stiffer than a single-ply braid. Braids can be one-ply, two-ply, three-ply, or more. Braids with more wires will be stiffer than those with fewer wires, and braids with wider diameter wires will be stiffer than those with narrow diameter wires. Wires of varying diameters can be used within the same braid 9.

The design of the braided assemblies 102 disclosed herein may vary based on whether the device 1 is intended for an arterial procedure or for a venous procedure, since the procedure site will be wider in a venous setting. For example, a braid 9 designed for a venous application may have a $d_{max}$ of from about 0.8 inches to 1.2 inches, including about 0.8 inches, about 0.9 inches, about 1.0 inch, about 1.1 inches, and about 1.2 inches. For venous applications, a braid 9 may have a wire diameter range from about 0.005 inches to about 0.02 inches, including 0.005 inches, 0.0075 inches, 0.01 inches, 0.0125 inches, 0.015 inches, 0.0175 inches, and 0.02 inches. Different wires of the braid 9 may have different diameters, or they may have the same diameter. In some venous implementations, the diameters of the wires of the braid 9 are 0.01 inches, 0.0125 inches, and/or 0.015 inches. Two-ply braids can utilize smaller wire diameters without sacrificing the radial force that can be applied. The pic count can be from 2 to 6 for venous applications. In some implementations used in venous applications, the pic count is 3, 4, or 5. The number of wires per braid for a venous application can be anywhere from 8 to 40, including 8, 16, 24, 32, and 40.

Braids for venous applications were tested using a selection of the above listed venous application parameters. End points included the expansion force and the radial outward force applied by the braid to the inner surface of a tubing that simulates a vein (the tubing having an inner diameter of 24 millimeters). The expansion force is the force required to open the braid, as applied to the activation wire. The data is shown below in Table 1.

TABLE 1

Prototype testing for braids used in venous applications

| Prototype | Braid Ply | Wire Diameter (Inches) | # of Wires | Maximum Braid OD (inches) | Radial Outward Force in 24 mm ID tube (N) | Expansion force (N) |
|---|---|---|---|---|---|---|
| A | Double | 0.008 | 16 per ply (32 total) | 1.0 | 4.4 | 2.5 |
| B | Double | 0.010 | 16 per ply (32 total) | 1.0 | 5.5-6.6 | 6 |
| C | Single | 0.0125 | 24 | 1.0 | 8.6-9.9 | 10 |

For arterial applications, the braid 9 can have $d_{max}$ of from about 0.1 inches to about 0.4, including about 0.1 inches, about 0.12 inches, about 0.14 inches, about 0.18 inches, about 0.2 inches, about 0.22 inches, about 0.24 inches, about 0.28 inches, about 0.3 inches, about 0.32 inches, about 0.34 inches, about 0.36 inches, about 0.38 inches and about 0.4 inches. For example, the braid 9 can have a $d_{max}$ of about 0.28 inches, 0.3 inches, or 0.31 inches. The diameter of the wires of the braid 9 for an arterial application can range from about 0.001 inches to about 0.007 inches, including about 0.001 inches, about 0.002 inches, about 0.003 inches, about 0.004 inches, about 0.005 inches, about 0.006 inches, and about 0.007 inches. Different wires of the braid 9 may have different diameters, or they may have the same diameter. In some arterial implementations, the diameters of the wires of braid 9 are 0.003 inches, 0.004 inches and/or 0.005 inches. Two-ply braids can utilize smaller wire diameters without sacrificing the radial force that can be applied. The pic count can be from 5 to 30 for arterial applications, including a pic count of 5, 6, 7, 8, 9, 10, 11, 12, 13, 14, 15, 16, 117, 18, 19, 20, 21, 22, 23, 24, 25, 26, 27, 28, 29 and 30. In some implementations used in arterial applications, the pic count is 10, 12, or 15. The number of wires per braid 9 for an arterial application can be anywhere from 8 to 54, including 8, 16, 24, 32, 40, 48, and 54. In some implementations, the number of wires per braid 9 for an arterial application is 26, 24, or 30.

Braids for arterial applications were tested using a selection of the above listed arterial application parameters. End points included the radial outward force applied by the braid to the inner surface of a tubing (the tubing having an inner diameter of 6 millimeters), and the proximal force needed to pull the braid through a restriction in the tubing (the inner diameter of the restriction being 4 millimeters). The tubing and the restriction simulate an artery and a thrombus/plaque, respectively. Favorable prototypes give a high radial outward force without requiring excessive force to pull the braid through the restriction. The data is shown below in Table 2. All braids tested were one-ply.

TABLE 2

Prototype testing for braids used in arterial applications

| Prototype | Wire Diameter (inches) | Pic count | # of Wires | Profile (Distal bond OD) (inches) | Maximum Braid OD (inches) | Radial Outward Force applied to 6 mm I.D. tubing (Newtons) | Force to pull through 4 mm ID Restriction (Newtons) |
|---|---|---|---|---|---|---|---|
| A | 0.004 | 10 | 16 | 0.050 | 0.28 | 0.8 | 1.8 |
| B | 0.004 | 15 | 24 | 0.053 | 0.28 | 1.0 | 2.8 |
| C | 0.005 | 10 | 16 | 0.054 | 0.31 | 1.5 | 3.2 |
| D | 0.005 | 10 | 24 | 0.058 | 0.31 | 1.6 | 4.1 |
| E | 0.006 | 10 | 16 | 0.060 | 0.31 | 1.7 | 4.4 |
| F | 0.006 | 12 | 16 | 0.063 | 0.30 | 1.8 | 4.6 |
| G | 0.002 | 24 | 48 | 0.073 | 0.31 | 0.8 | 1.9 |
| H | 0.003 | 24 | 48 | 0.078 | 0.31 | 1.8 | 3.5 |
| I | 0.004 | 12 | 24 | 0.054 | 0.31 | 1.9 | 2.6 |

The activation wire 105 extends through the lumen of the retrieval device 3, exits the retrieval device 3 at exit point 11, and extends distally along the exterior surface of the retrieval device 3. The distal end 13 of the activation wire 105 is attached to slidable collar 108. As such, the activation wire 105 is able to control the expansion and collapse of the braid 9 via the slidable collar 108. The distance between exit point 11 and slidable collar 108 affects the length that the slidable collar can be pulled along retrieval device 3 to open the braided assembly 102. If it is too close to slidable collar, the braided assembly 102 will not be able to open fully. As such, exit point 11 should be positioned proximally far enough from the unexpanded position of slidable collar 108 to enable the braided assembly 102 to open to its maximum outer diameter. FIG. 1C shows the implementation of FIGS. 1A and 1B without braid 9 to facilitate viewing the activation wire 105 and the activation wire exit point 11. FIG. 1D is a cross sectional view of activation wire 105 in retrieval device 3, taken at line A-A of FIG. 1C. The internal positioning of the proximal regions of the activation wire 105 (within retrieval device 3) is advantageous in that no friction or bulk is added by the system that controls expansion of the braided assembly 102.

The proximal region of activation wire 105 (not shown) may be tensioned and released to control the expansion and collapse of the braided assembly 102 via movement of slidable collar 108. Under tension, the activation wire 105 moves proximally within the lumen of the retrieval device 3 as it translates the tension from the proximal region of the activation wire 105 to the braided assembly 102. In implementations where the slidable collar 108 is in the distal position (as shown), the exit point 11 of the activation wire is located proximally to the slidable collar 108. The exit point 11 can be, for example, a portal in the sidewall of retrieval device 3. Use of a slidable collar 108 to expand the braided assembly 102 is advantageous because the distal end of the braided assembly 102 can be moved while the distal region 5 of the retrieval device 3 maintains a constant position within the vasculature. Maintaining a constant position of the distal region 5 of retrieval device 3 is advantageous because sliding proximal/distal movement of the distal region 5 within the vessel can result in vessel damage or perforation.

In implementations where the slidable collar 108 is in the proximal position relative to the fixed attachment point (not shown), the activation wire 105 extends distally past the slidable collar 108 inside the retrieval device 3, exits the retrieval device 3 at exit point 11, then doubles back and extends along the exterior surface of the retrieval device 3 to attach to the proximally located slidable collar 108. The exit point 11 can be a portal in the sidewall of the retrieval device as described above, or the exit point 11 can be the distal end 107 of the retrieval device 3.

Retrieval device 3 can include a proximal hypotube 100 and a distal support tube 104, as shown in FIG. 1C. In some implementations, the hypotube 100 extends through the support tube 104. However, the distal region can be made more flexible by attaching the proximal end of the distal support tube 104 to the distal end 17 of the proximal hypotube 100 (for example, by adhesive bonding, heat bonding, or welding processes). The fixed attachment point 101 of the braided assembly 102 can be located on distal support tube 104 and the slidable collar 108 can extend around the distal support tube 104, such that the braided assembly 102 is positioned over and around the distal support tube 104. The braided assembly 102 can alternatively be positioned only partially over the distal support tube (i.e., one of the fixed attachment point 101 or the slidable collar 108 is attached to the proximal hypotube 100, and the other of the fixed attachment point or the slidable collar 108 is attached to the distal support tube 104). In some implementations, the support tube 104 serves to increase the overall diameter of the retrieval device 3, for example, to accommodate a larger diameter braid and to encapsulate the guidewire tip 103. The distal support tube 104 can also provide a lower friction surface for movement of the slidable collar 108 than the proximal hypotube 100 would provide.

In some implementations, distal support tube 104 has greater flexibility than the proximal hypotube 100. For example, the distal support tube 104 can be made of a polymer material, while the proximal hypotube 100 is made of a more rigid metal material. In some implementations, the proximal hypotube 100 is constructed from metal hypodermic needle tubing. The hypotube 100 can be up to 50 times stiffer than the support tube 104. There are several advantages to having a distal support tube 104 with greater flexibility than proximal hypotube 100. The greater flexibility of the support tube 104 enables a gradual transition in flexibility between the hypotube 100 and the guidewire tip 103. In some scenarios, the greater flexibility of the distal support tube 104 can facilitate movement of the braided assembly 102 through a tortuous thrombus. The greater flexibility can promote kink resistance. The greater flexibility of the distal support tube 104 can also facilitate the introduction of a portal or exit point 11 during the production of the device. The higher rigidity of the hypotube 100 (as compared to support tube 104) is important because it allows the retrieval device 3 to be pushed through the vasculature. The rigidity of hypotube 100 also helps to ensure that the braided assembly 102 can be pushed through a thrombus or plaque.

On the proximal end, the activation wire 105 can be attached to a tensioning element (not shown) that allows the activation wire 105 to be moved forward or retracted backward within the retrieval device 3. Applying tension to the activation wire 105 causes the slidable collar 108 to move and causes the braided assembly 102 to expand to a diameter of the practitioner's choosing. Similarly, releasing tension on the activation wire 105 allows the braided assembly 102 to relax into the collapsed, baseline configuration.

In some implementations, such as the one shown in FIG. 2, the device includes a proximal handle 128. The handle 128 is coupled to a proximal end of retrieval device 3. The tensioning element is a knob 129 that is coupled to the proximal end of activation wire 105 on the inside of the handle. Actuation of the knob 129 in one direction causes the activation wire 105 to be tensioned (expanding the braided assembly), and actuation of the knob 129 in the opposite direction releases tension on the activation wire 105 (collapsing the braided assembly). In other implementations, the tensioning element can include a slider, ratcheting mechanism, or lever.

Figure 8:
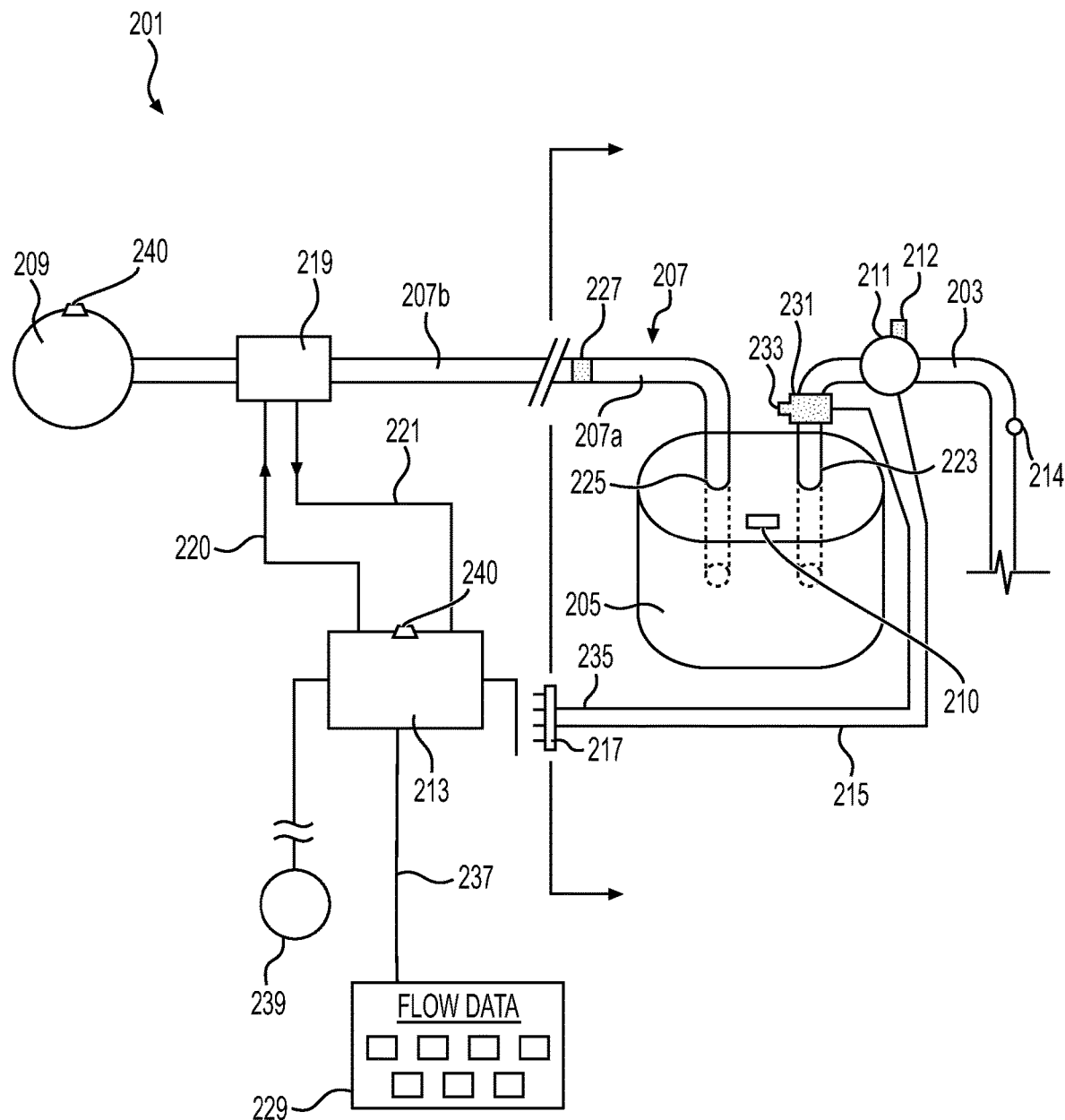
FIG. 8 is a diagram of an aspiration system for controlling blood loss during thrombus removal.
Figure 13:
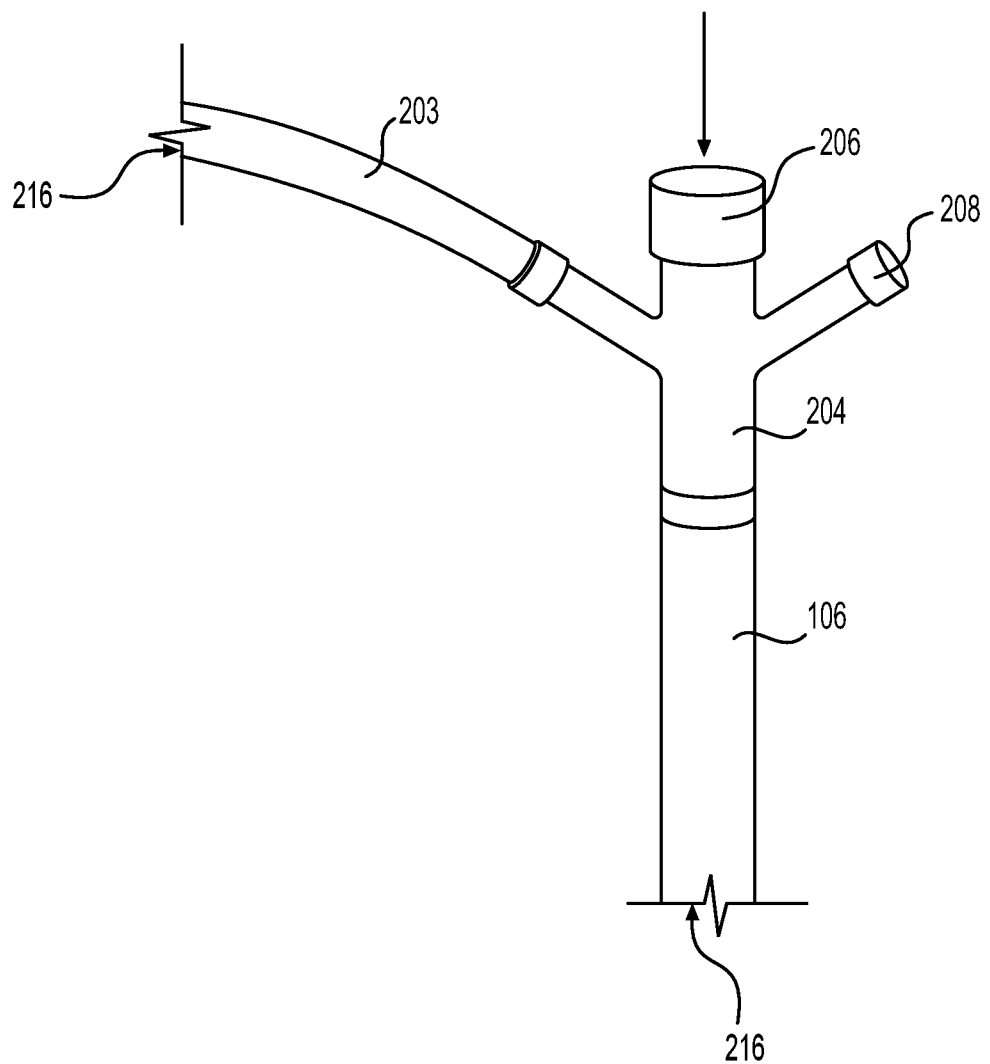
FIG. 13 shows a proximal end of an aspiration catheter connected via an adapter to an aspiration tubing.

In some implementations, aspiration catheter 106 terminates in an adapter, such as adapter 204 shown in FIG. 13. The adapter 204 facilitates the connection of aspiration tubing 203, which can be connected to a vacuum system such as shown in FIG. 8 for removal of the clot or emboli. In some exemplary procedures, the distal end of retrieval device 3 is inserted axially through into the proximal end of adapter 204 (where shown using the arrow in FIG. 13). The retrieval device 3 is slid through the adapter 204 and subsequently through the aspiration catheter 106 until handle 128 abuts the proximal end of adapter 204.

Figure 7A:
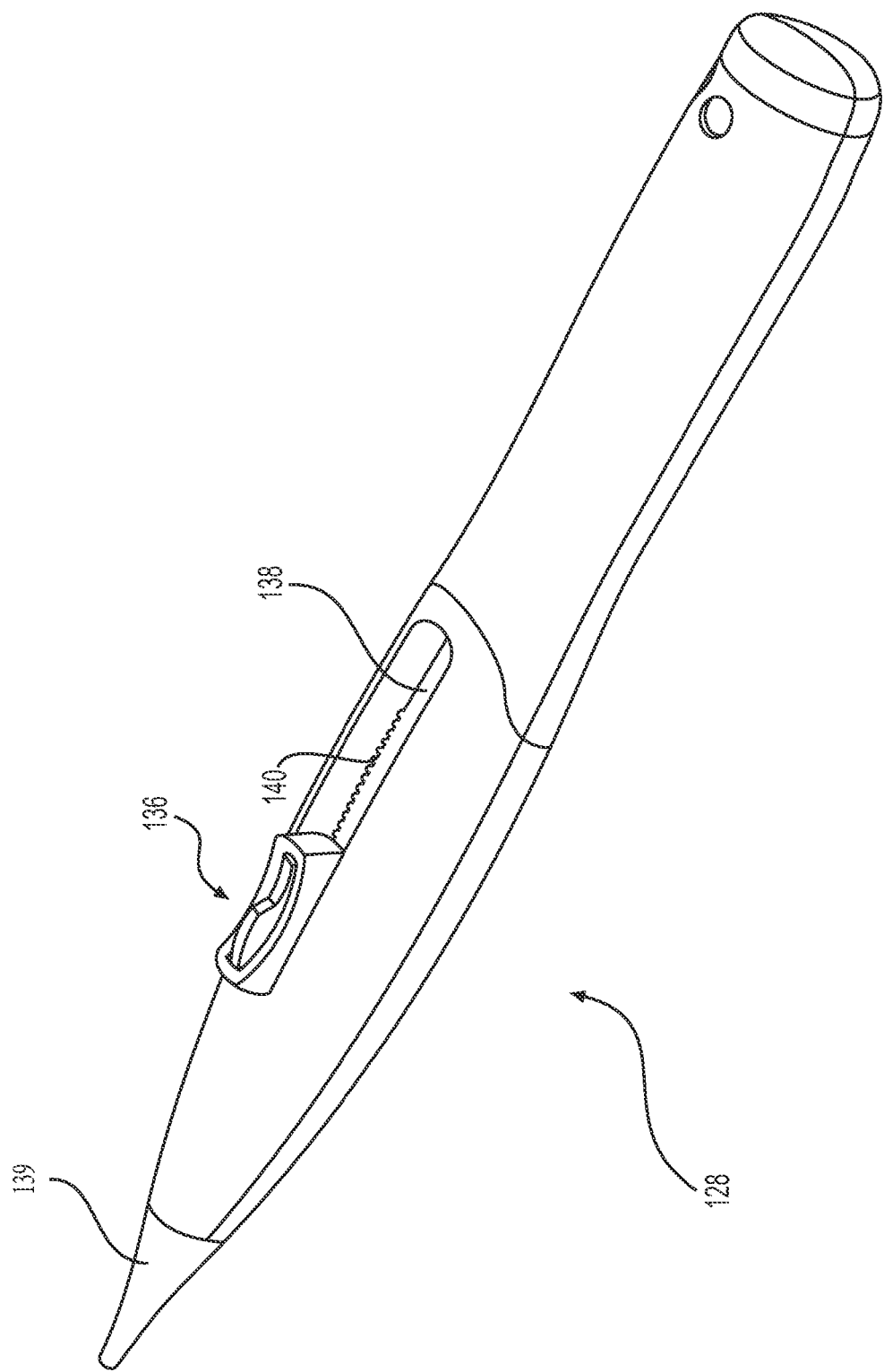
FIG. 7A shows a perspective view of another implementation of a handle that can be used to control expansion and retraction of a braided assembly.
Figure 7C:
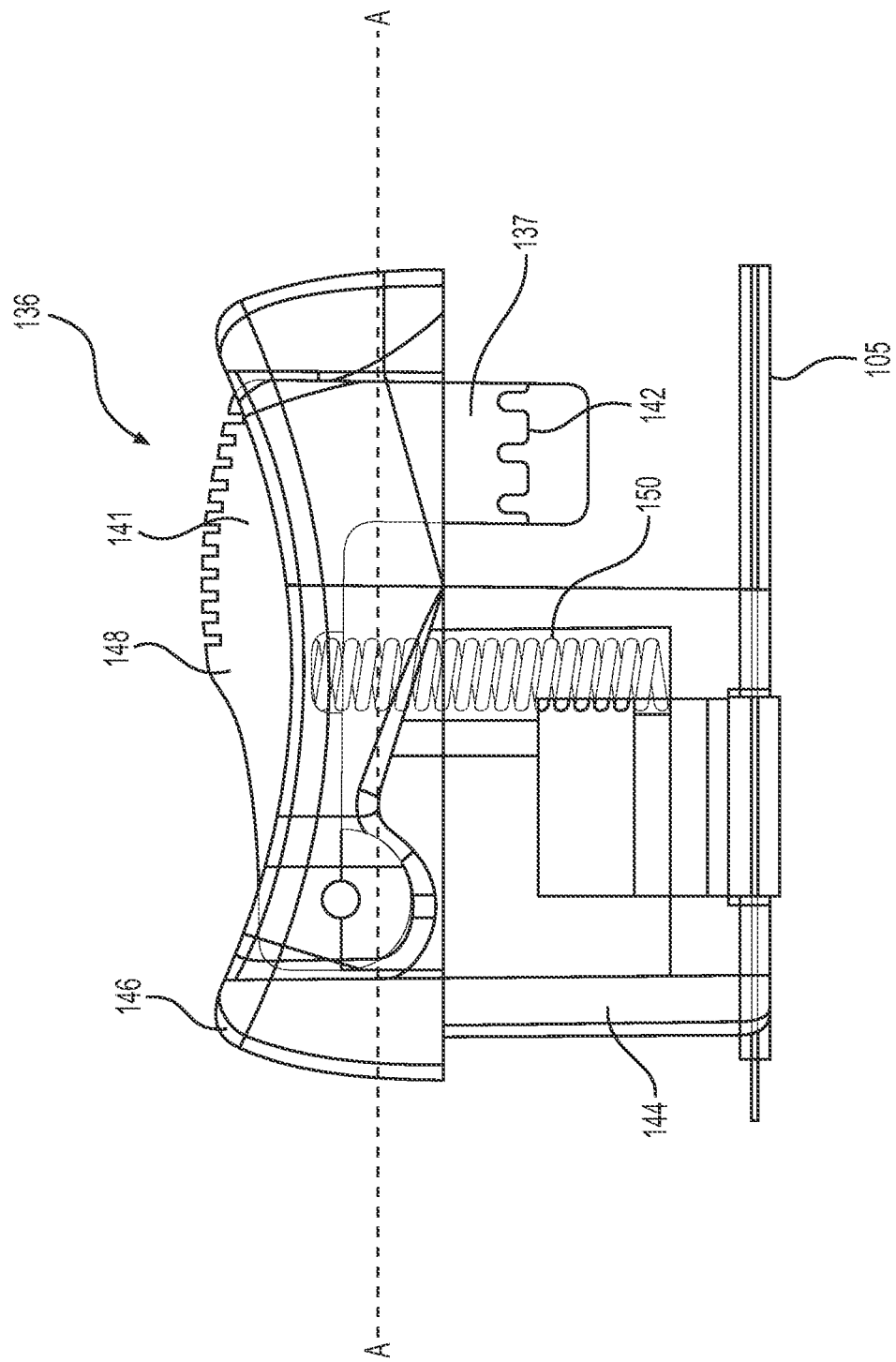
FIG. 7C shows a cross section of the locking slider circled in FIG. 7B.

Another implementation of a proximal handle 128 is shown in FIGS. 7A-7C. The handle 128 of FIGS. 7A-7C is advantageous in that it enables a practitioner to lock the braided assembly 102 at a fixed outer diameter. This can be useful, for example, when pushing and pulling the device through a thrombus. As shown in FIG. 7A, proximal handle 128 is coupled to a proximal end of retrieval device 3. Activation wire 105 extends proximally past the proximal end retrieval device 3 and into proximal handle 128. Strain relief section 139 is formed of a flexible material that prevents kinking of the retrieval device 3 just distal to the handle 128. Proximal handle 128 also includes a tensioning element in the form of locking slider 136, which slides proximally and distally within groove 138 and can be locked in place to secure the outer diameter of the braided assembly 102 during a procedure. The underside of locking slider 136 and groove 138 is shown in FIG. 7B, and a cross sectional view of locking slider and groove 138 is shown in FIG. 7C. Locking slider 136 includes a sliding portion 146 and a lock button 148. As seen in FIG. 7B, downward pointing teeth 140 extend downward from the inner surface 133 of the outer casing 135 of handle 128, from a position adjacent the groove 138. The lock button 148 includes an exterior portion 141 with a textured gripping surface. The lock button 148 extends downward through sliding portion 146, and includes an interior portion 137. The interior portion 137 of the lock button 148 extends away from the exterior portion 141 of lock button 148 in a direction that is perpendicular to the longitudinal axis A-A of the locking slider 136. Interior portion 137 includes upward facing teeth 142 that are configured to engage with the downward facing teeth 140 of the outer casing 135 of the handle 136. Spring 150, which is vertically positioned within slider 146, beneath the exterior surface 141 of lock button 148, exerts an upward force on lock button 148 to hold the upward facing teeth 142 in a locked configuration with the downward facing teeth 140 of the outer casing 135. When lock button 148 is compressed, the spring 150 is compressed and the teeth 140, 142 disengage. With the lock button 148 pressed and the teeth 140, 142 disengaged, proximal or distal force can be applied to sliding portion 146 to move the locking slider 136 within the groove 138. An interior portion 144 of the sliding portion 146 grips the activation wire 105. As the locking slider 136 is moved within groove 138, the activation wire 105 is moved proximally or distally to affect the expansion or allow the collapse of the braided assembly 102.

Conventional thrombectomy devices utilize shape memory elements with a baseline expanded configuration. These conventional devices risk inadvertent overexpansion and damage to the vessel. Furthermore, conventional devices are often restrained by a bulky overlying sheath, which is pulled back to allow the device to self-expand.

Advantageously, using a device with a shape memory of the collapsed position reduces the risk of overexpansion and injury during self-expansion. Self-collapse also allows the device to be restrained using the low-profile activation wire system described herein. An additional advantage is the ability to expand the braided assembly to various diameters to precisely custom fit the size of the vessel. This can be especially useful if the size of the vessel is different than originally anticipated. The level of grip between the braid 9 and the surrounding thrombus can also be customized as needed by applying different levels of tension to the activation wire 105. For example, the practitioner may apply a first level of tension to deploy the braided assembly 102 to a first expanded outer diameter to contact the thrombus. If the force between the thrombus and the braid 9 is not enough to pull the thrombus toward the aspiration catheter 106, the practitioner can widen the braid 9 to a second expanded outer diameter by applying a greater second level of tension to the activation wire 105. This widened diameter provides a greater contact force between the thrombus and the braid 9, such that the thrombus can be more easily pulled toward aspiration catheter 106.

Figure 3A:
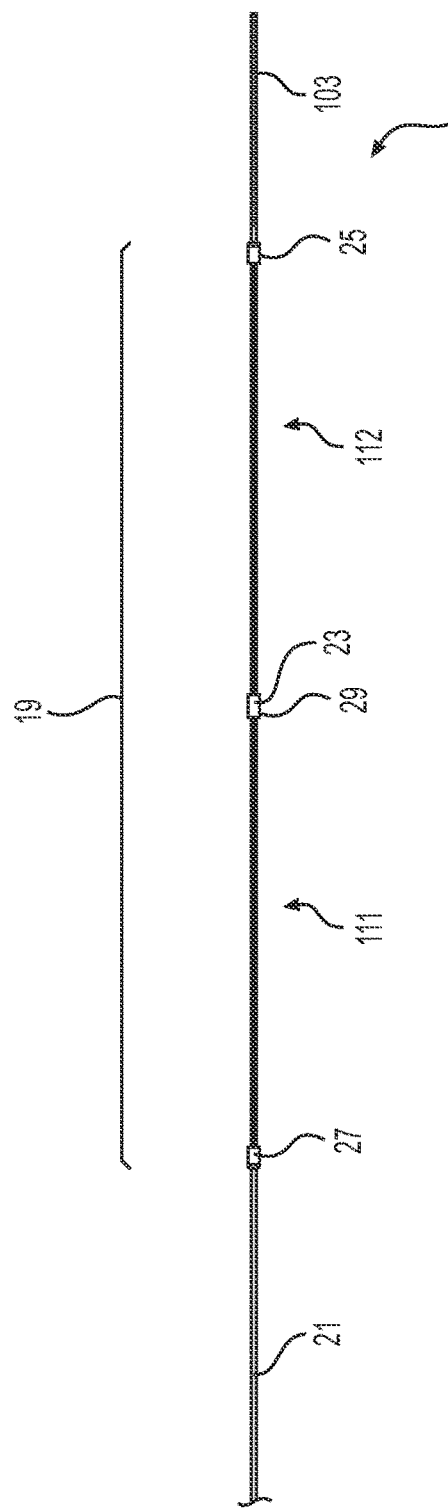
FIG. 3A is a side view of a distal region of an additional implementation of the thrombectomy device in an unexpanded configuration. The implementation has a braided assembly having multiple braided sections.
Figure 3B:
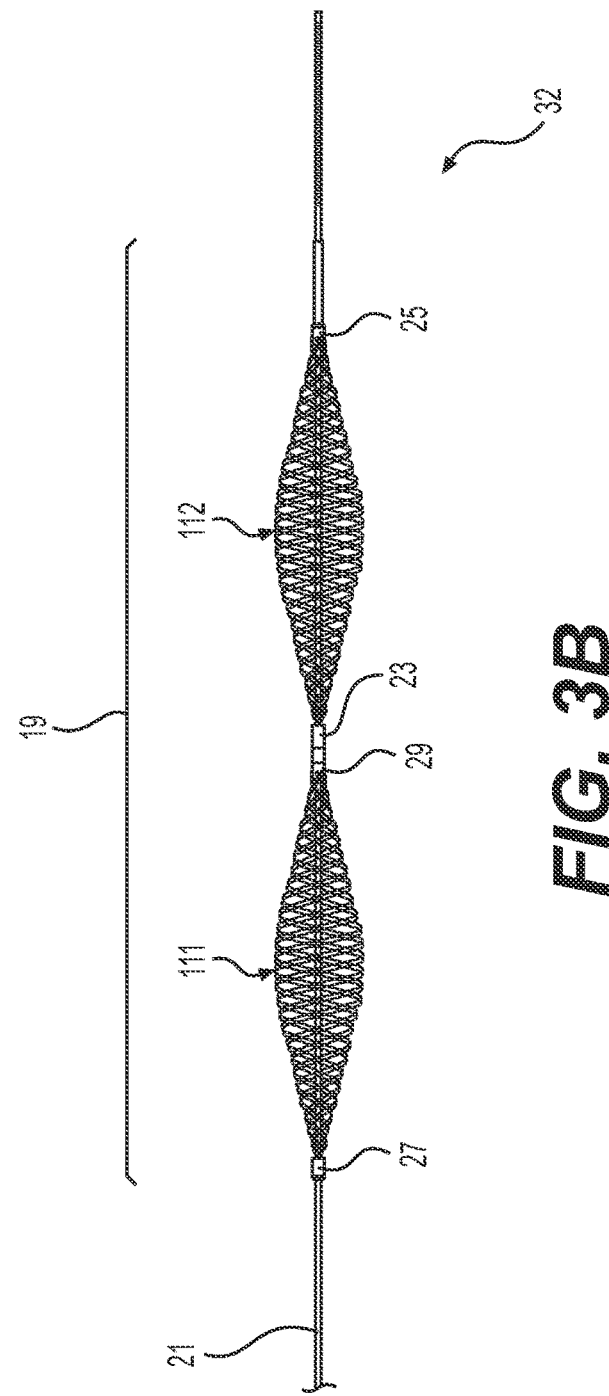
FIG. 3B is a side view of the distal region of the implementation of FIG. 3A in an expanded configuration.

FIGS. 3A-3D show an additional implementation of a thrombectomy device having a braided assembly 19 with multiple braided sections 111, 112. The elongated nature of this implementation facilitates the capture and retrieval of long thrombi. As shown in FIG. 3A and FIG. 3B, ach of the braided sections 111, 112 is attached to and extends around the distal region 22 of retrieval device 21. The braided assembly 19 includes multiple sliding collars 23, 25 and a fixed attachment point 27. Proximal braided section 111 is attached to and extends between the fixed attachment point 27 and the proximal slidable collar 23, where it is welded, bonded, or otherwise adhered at a central sliding attachment point 29. Distal braided section 112 is attached to and extends between the proximal slidable collar 23 and the distal slidable collar 25. In some implementations, the braided sections are formed by constraining one larger braid with the proximal slidable collar 23. In other implementations, each braided section is formed from a separate braid (such that each of the proximal and distal braided assemblies are separately fixedly attached to proximal slidable collar 23). In some implementations, the slidable collars 23, 25 can be positioned distally to the fixed attachment point 27, as illustrated in FIG. 3A. In other implementations, the slidable collars can be positioned proximally to the fixed attachment point (not shown). Though illustrated with two braided sections 111, 112, other implementations of the braided assembly 19 could include more than two braided sections and more than two slidable collars.

FIG. 3C shows the thrombectomy device of FIGS. 3A and 3B without the braided assembly 19. Retrieval device 21 has a hypotube 131 fixedly attached to a support tube 130. A single activation wire 132 extends through hypotube 131 and support tube 130 to an exit point 134 positioned on the support tube 130. From there, it travels along the outer surface of support tube 130, running beneath proximal sliding collar 23 to attach to distal sliding collar 25. Cross sectional views shown in FIG. 3D, FIG. 3E, FIG. 3F, and FIG. 3G show the radial position of activation wire 132 with respect to hypotube 131, the support tube 130, and the guidewire tip 103 at various axial locations along the thrombectomy device shown in FIG. 3C. The activation wire 132 is utilized to control expansion of the braided assembly via connection to the distal sliding collar 25. In other implementations, the activation wire 132 can be attached to the proximal sliding collar 23. Proximal movement of the proximal slidable collar 23 or the distal slidable collar 25 by the activation wire generates a force on the other of the two slidable collars, such that the two braided sections 111, 112 are expanded (or partially expanded) in unison. As described above, the braids are formed of a shape memory material with a bias toward the collapsed configuration, so that tensioning the activation wire enables multiple levels of expansion.

FIG. 4 shows an additional implementation with multiple, separately expandable braided assemblies 37, 39. The braided assemblies 37, 39 are spaced from each other along the distal region 32 of retrieval device 31. The proximal braided assembly 37 includes braided section 113 that extends between a fixed attachment point 33 and a slidable collar 115. The distal braided assembly 39 includes braided section 114 that extends between a fixed attachment point 35 and a slidable collar 116. Each braided assembly is controlled by a separate activation wire, such that each braided assembly can be individually controlled. Each activation wire exits the retrieval device 31 from an exit point beneath the individual braid and attaches to the individual slidable collar (not shown). The multiple activation wires can travel through the same lumen in retrieval device 31, or they could have individual lumens. Depending upon the positioning of the slidable collars in relation to the fixed attachment points, in some implementations, each additional activation wire can travel through the same lumen and exit the retrieval device at the same portal, or at different portals. In some implementations, one or more activation wires can exit from the distal end of the retrieval device 31.

As with the previously described implementations, the braids of the implementation shown in FIG. 4 are formed of a shape memory material with a bias toward the collapsed configuration, such that tensioning the activation wire enables deployment of the braid to a range of diameters. Each braided assembly is deployable to a partially expanded configuration by placing a first level of tension in the attached activation wire, or to a fully expanded configuration by placing a second, greater level of tension into the activation wire. Thus, when multiple activation wires and braided assemblies are used, a first braided assembly can be deployed to a partially expanded state while a second braided assembly is deployed in a fully expanded state. In some scenarios, it may be advantageous for one braided assembly to be fully collapsed while another braided assembly is either partially or fully expanded. This can be advantageous, for example, when pulling a longer thrombus into the aspiration catheter 106. The proximal braided section 113 can be collapsed as it enters the aspiration catheter, prior to the distal braided section 114 which is still outside of the aspiration catheter.

In some implementations, braids of separate braided sections or separate braided assemblies can have different properties, such as different maximum expanded diameters, different wire sizes, different wire densities, different numbers of wires, etc. These properties can vary depending upon the positioning of the braided section or the braided assembly along the retrieval device. For example, the distal braided section or braided assembly might have a larger expanded diameter to better pull back against the thrombus, while the proximal braided section(s) or braided assembly(s) might be less dense and stronger to better engage the middle of the thrombus.

Figure 5A:
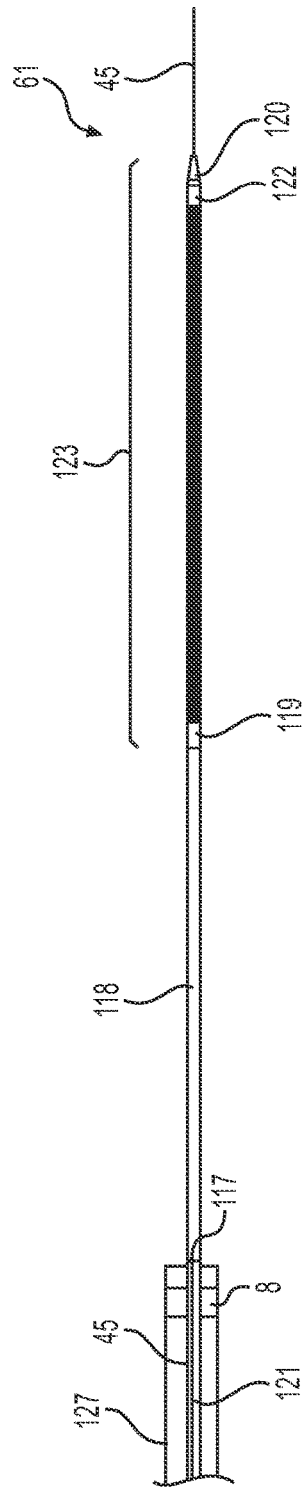
FIG. 5A shows a side section view of an implementation of the thrombectomy device that enables use with a guidewire.
Figure 5B:
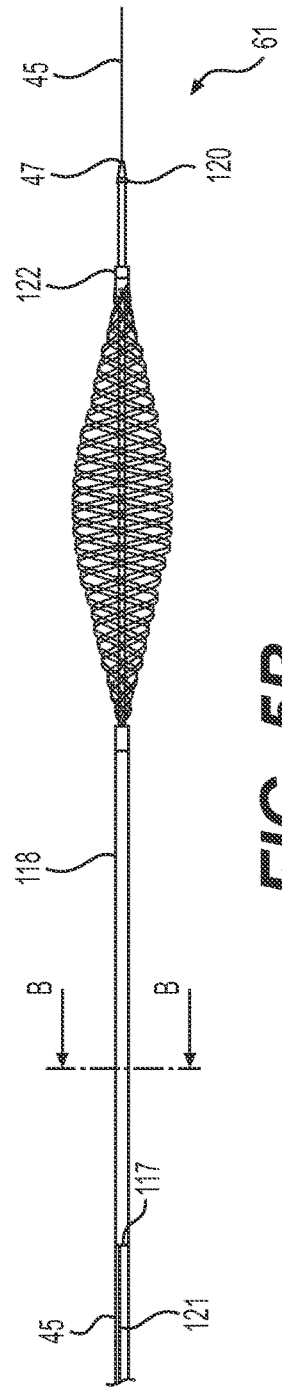
FIG. 5B shows the implementation of FIG. 5A in an expanded configuration.
Figure 5C:
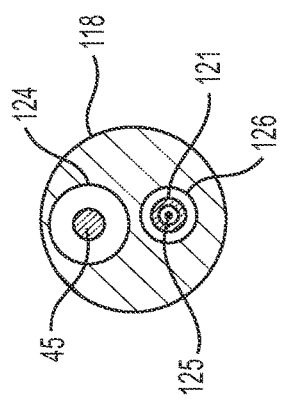
FIG. 5C is a cross section of the implementation of FIGS. 5A and 5B, taken along line B-B of FIG. 5B.

FIGS. 5A-5C show an implementation of the thrombectomy device that enables use with a guidewire, such that a practitioner can remove and reinsert the device to the same anatomic position multiple times (for example, to clean the device during the procedure). FIG. 5A shows aspiration catheter 127, retrieval device 121, guidewire tubing 118, braided assembly 123 (in the collapsed configuration), and guidewire 45. Guidewire tubing 118 is positioned around the distal region 61 of retrieval device 121. The guidewire tubing 118 is shorter than the retrieval device 121 in the longitudinal direction, such that the guidewire 45 leaves the guidewire tubing 118 at the proximal guidewire exit 117 and extends alongside retrieval device in a proximal direction. FIG. 5B shows the implementation of FIG. 5A with the braided assembly 123 in an expanded state. As shown in the cross section of FIG. 5C taken at line B-B of FIG. 5B, guidewire 45 extends through the first lumen 124 of the guidewire tubing 118. The guidewire 45 exits guidewire tubing 118 at distal guidewire exit 47. The guidewire tubing 118 can include a distal atraumatic tip 120. The guidewire tubing 118 can be formed, for example, of a polymer material. Retrieval device 121, including activation wire 125, extends through a second lumen 126 of the guidewire tubing 118. As described above, the activation wire 125 is connected on the proximal end to a tensioning element, extends through retrieval device 121 to an exit point, leaves the retrieval device 121 at the exit point (beneath the braid), and attaches at its distal end to the slidable distal collar 122 on the braided assembly 123. The exit point can be, for example, a tunnel through the sidewalls of the retrieval device 121 and the guidewire tubing 118 (i.e., a tunnel formed by a portal in the sidewall of the retrieval device 121 that is aligned/coaxial with a portal in the sidewall of the guidewire tubing 118). In use, the guidewire tubing 118 and the retrieval device 121 are introduced together over the previously placed vascular guidewire 45. Because the guidewire 45 is retained within the guidewire tubing 118, it is pulled at least partially to the side within the lumen of aspiration catheter 127 and can move without interfering with activation wire 125. The guidewire tubing 118 and the retrieval device 121 keep the activation wire 125 and the guidewire 45 moving in an axial direction, independently from one another, using a low-profile and low-friction design. Once in position, the braided assembly 123 is expanded and the proximal end of the aspiration catheter 127 is connected to a vacuum source. The braided assembly 123 is expanded and then retracted back toward the aspiration catheter 127, pulling the clot with it and breaking it into small pieces.

Figure 6A:
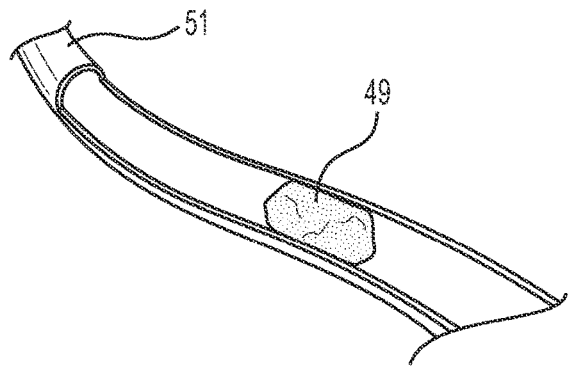
FIGS. 6A-6F show an example method of using a thrombectomy device.

Methods of performing thrombectomy procedures are also disclosed herein. An example method is illustrated in FIGS. 6A-6F. FIG. 6A illustrates thrombus 49 occluding vessel 51. Distal end of aspiration catheter 53 is advanced through the vasculature to an area proximal to the thrombus 49, as shown in FIG. 6B. The distal end of retrieval device 55 carrying braided assembly 57 is advanced out the distal end of the aspiration catheter 53 and through thrombus 49, such that the braided assembly 57 is distal to thrombus 49, as shown in FIG. 6C. The practitioner then places tension in the activation wire housed inside the retrieval device 55, thereby moving the activation wire longitudinally within the lumen of the retrieval device and moving the slidable collar of the braided assembly longitudinally over the exterior surface of the retrieval device. Movement of the slidable collar via the activation wire causes braided assembly 57 to expand to the diameter of the practitioner's choosing. Should the practitioner wish to alter the level of expansion during the procedure (i.e., change the maximum diameter d of the braided assembly 57), this is made possible by altering the level of tension in the activation wire, which again moves the activation wire within the retrieval device and moves the slidable collar, as described above. Advantageously, the distal end of the retrieval device 55 maintains a stationary position as the braided assembly is expanded to the optimal diameter. Maintaining a constant position of the distal end of retrieval device 55 is advantageous because sliding proximal/distal movement of the distal end within the vessel can result in vessel damage or perforation.

Figure 6D:
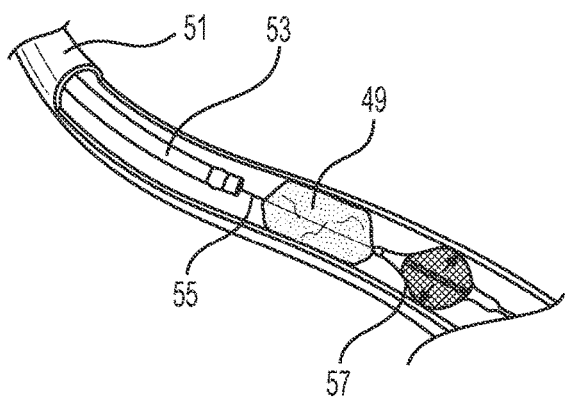
Figure 6B:
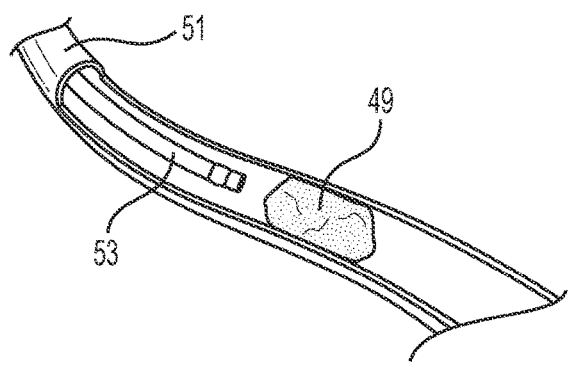
Figure 6E:
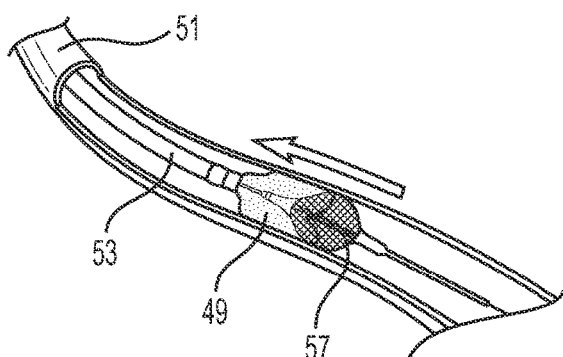
Figure 6C:
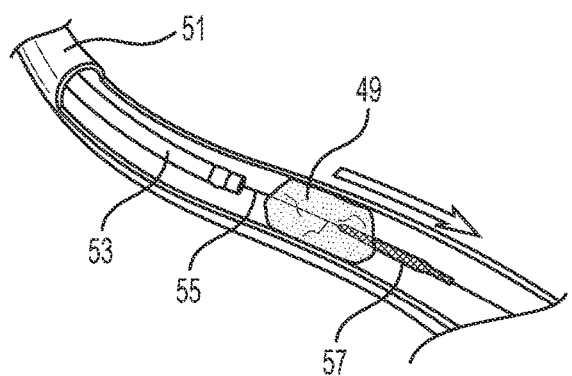
Figure 6F:
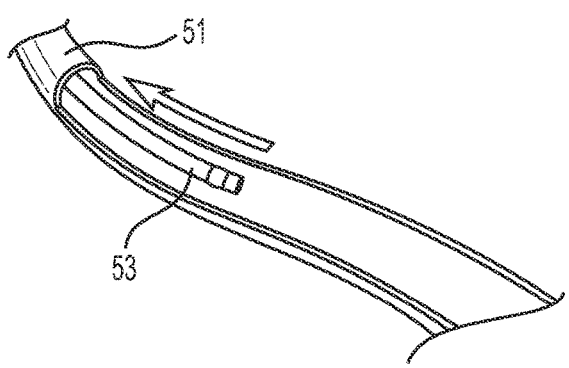

FIG. 6D shows the braided assembly 57 in an expanded configuration, sized to fit the vessel 51. The practitioner then pulls the retrieval device 55 proximally and contacts the thrombus 49 with the braided assembly 57, as shown in FIG. 6E. The thrombus 49 and braided assembly 57 are pulled proximally toward aspiration catheter 53. The aspiration catheter 53 can be connected to an external vacuum source (not shown), which enables the aspiration of the thrombus 49 into the distal end of the aspiration catheter 53. The aspiration catheter 53 is then retracted proximally, as illustrated in FIG. 6F, and removed from the body.

The ability to open the braided assembly to a range of different diameters is useful to thrombectomy procedures for multiple reasons and in multiple scenarios. The ability to custom fit the braid to a particular vessel during the procedure is preferable over introducing a braid that expands to a predetermined size, then discovering mid-procedure that it is either too small to grip the thrombus or that it is too large and has damaged the vessel. As another exemplary advantage, the level of grip between the braid and the thrombus can be optimized mid-procedure. For example, the practitioner may apply a first level of tension to the activation wire to deploy the braided assembly to a first expanded outer diameter to contact the thrombus. If the force between the thrombus and the braid is not sufficient to pull the thrombus toward the aspiration catheter, the practitioner can widen the braid to a second expanded outer diameter by applying a greater second level of tension to the activation wire. This widened diameter increases the contact force between the thrombus and the braid, such that the thrombus is more easily pulled toward aspiration catheter.

The methods can also be performed using a guidewire. For example, the guidewire can be positioned distal to the thrombus prior to advancing the distal end of the retrieval device. The retrieval device extends at least partially through a lumen of the guidewire tubing, such as in the implementation of FIGS. 5A-5C. Together, the retrieval device and guidewire tubing are advanced over the guidewire and toward the thrombus. The guidewire extends through a separate lumen of the guidewire tubing than the retrieval device and activation wire. Once positioned, the activation wire is moved longitudinally within the retrieval device to expand the braided assembly.

Long thrombi can be addressed using braided assemblies with multiple braided sections such as the implementation shown in FIG. 3. Movement of the slidable collar results in expansion of more than one of the braided sections, resulting in a relatively long braided assembly. In some implementations a device with multiple, separately expandable braided assemblies, such as the one shown in FIG. 4, can be used to treat long thrombi. With separately expandable braided assemblies, as the thrombus is drawn proximally closer to the distal end of the aspiration catheter, the proximally positioned braided assembly collapses from a first expanded outer diameter to the collapsed diameter (or to a narrower second expanded outer diameter). The distally positioned braided assembly maintains an expanded outer diameter that is greater than the outer diameter of the proximally positioned braided assembly until it too is pulled into the aspiration catheter.

The aspiration systems and methods disclosed herein are configured to control blood loss during thrombus removal. An example aspiration system 201 is shown in FIG. 8. The aspiration system 201 includes an aspiration tubing 203, which extends from adapter 204 shown in FIG. 13. An aspiration lumen 216 extends from (and includes) the lumen of the aspiration catheter 106 and the lumen of the aspiration tubing 203 leading to the receptacle 205. The aspiration tubing 203 is coupled to a receptacle 205 for collecting liquid aspirated by the aspiration catheter 106. In other implementations, aspiration catheter 106 can be directly coupled to receptacle 205 for collecting liquid aspirated by the aspiration catheter 106. The aspiration tubing 203 (or aspiration catheter 106) creates a fluidic seal with the receptacle 205, and a vacuum line 207 is also fluidically coupled to and sealed with receptacle 205. The vacuum line 207 is fluidically coupled to a vacuum pump 209.

The aspiration tubing 203 is coupled to one or more sensors 211. (If aspiration catheter 106 is directly attached to receptacle 205, the sensors 211 are coupled to the catheter 106.) A sensor 211 is configured to measure a flow parameter associated with a liquid within the lumen of the aspiration tubing 203 (such as the flow rate, for example). The sensor 211 is operably connected to a vacuum controller 213, for example, via wiring 215 to 4-pin connector 217 (or any suitable connector). The vacuum controller 213 is also operably coupled to a regulator 219, for example, via wiring 220, and regulator 219 is coupled to vacuum line 207. The regulator 219 is configured to adjust the vacuum pressure within the vacuum line 207.

When the vacuum controller 213 receives the flow parameter from sensor 211, it compares the flow parameter to a desired target range and sends an automatic control signal to the regulator 219, based on the comparison of the flow parameter to the target range. The automatic control signal causes the regulator 219 to adjust the vacuum pressure within vacuum line 207. For example, the automatic control signal can cause the regulator 219 to reduce the vacuum pressure upon a determination that the flow parameter is above an upper limit of the target range, or to decrease the vacuum pressure upon a determination that the flow parameter is below a lower limit of the target range. The vacuum controller 213 and the regulator 219 can optionally communicate in a feedback loop to regulate the vacuum pressure, wherein the vacuum controller 213 communicates a control signal to the regulator 219 and the regulator 219 communicates the current vacuum pressure back to the vacuum controller 213. In one example, communication from the regulator 219 to the vacuum controller 213 can be accomplished via wiring 221. These components and operations will be discussed in greater detail, below.

The vacuum pump 209 can be a standard medical suction pump conventionally used in hospitals, outpatient surgery centers, and clinical practices. As one example, the vacuum pump 209 can be a Basic Suction Pump (Medela A G, Baar, Switzerland), which has piston-cylinder based drive unit and mechanical overflow to protect the pump. The Medela Basic Suction pump has a max flow rate of 300 mL/min and a maximum vacuum of 90 kPa below ambient pressure. However, the make or model of vacuum pump 209 is not limited—it can be any type available in clinical settings. The vacuum pump 209 can be provided by the user, or it can be provided as part of a kit with some or all of the other components shown in FIG. 8.

The aspiration tubing 203 is coupled to the receptacle 205 at an intake port 223, and the vacuum line 207 is coupled to the receptacle 205 at the vacuum port 225. The aspiration tubing 203, receptacle 205, and vacuum line 207 can be any make or model. The sizes and materials can be adapted to suit the needs of the particular procedure. These components can be provided by the user, or they can be provided as part of a kit with some or all of the other components shown in FIG. 8. The components shown on the right side of the arrows in FIG. 8, including the aspiration tubing 203, the flow sensor 211, the receptacle 205 and the vacuum line 207 can all optionally be disposable to reduce the need for sterilization between procedures. A connector 227 can be placed on the vacuum line 207 to enable connection of the disposal portion 207a of the vacuum line with a reusable portion 207b of the vacuum line.

As discussed above, regulator 219 communicates with vacuum controller 213 to control the pressure in vacuum line 207. In one example, the regulator is an ITC 2090. As one example, the regulator 219 include can have a valve that opens the vacuum line 207 to the atmosphere, thus decreasing the vacuum pressure by venting the system. As another example, regulation of flow can be achieved by incorporating an adjustable flow valve, which may widen or narrow the vacuum line 207b to alter the flow capacity (i.e., direct flow control). Notably, handling flow adjustments on the vacuum side (i.e., to the left of the arrow in FIG. 8) reduces the need to clean the flow handling components. This is an advantage over systems with components that physically restrict blood flow within the aspiration tubing.

The flow sensor 211 can be in direct contact with the liquid in the aspiration tubing 203, or it can be configured for contactless sensing. For example, in some implementations, the flow sensor 211 is a paddle-wheel style sensor positioned within the aspiration lumen 216. A paddle-wheel style sensor sends turn frequency measurements to the vacuum controller 213, which determines the flow rate accordingly. Alternatively, the flow sensor 211 can be an ultrasonic sensor, a laser-based sensor, an infrared sensor, or some other optical based sensor, measuring the flow parameters through the walls of aspiration tubing 203 without contacting the blood. These have the benefit of being reusable, but are typically costlier than a contact-based sensor. While a single sensor 211 is shown in FIG. 8, it is further possible to incorporate a plurality of sensors that measure at disparate points along a length of the aspiration tubing 203. In some examples, an interfacing filter can be positioned upstream from the flow sensor 211 to filter clots before they reach the sensor.

Adapter 204 shown in FIG. 13 facilitates the entry of the retrieval device 3 through proximal port 206 and into the lumen of the aspiration catheter 106. Adapter 204 also provides a fluidic coupling between the aspiration catheter 106 and vacuum system 201 (via aspiration tubing 203). Infusion port 208 allows for the introduction of saline or other infusion fluids. Adapter 204 houses an airtight valve that enables retrieval device 3 to be introduced through proximal port 206 without passing air into the adapter 204. However, the aspiration tubing 203 can include an air leak sensor 214, such as an optical sensor, to detect air passage in case of valve failure. In some implementations, the air leak sensor 214 is positioned proximal to the flow sensor 211 to detect air before it reaches the vacuum system. Alternatively, the air leak sensor 214 can be integral with the flow sensor 211.

The air leak sensor 214 can communicate a leak signal to the vacuum controller 213, the regulator 219, or directly to the vacuum pump 209, at which point the vacuum controller 213, the regulator 219, or the pump 209 slows or stops the vacuum flow while the air leak is addressed, reducing blood loss. In some implementations, there is a leak detection delay during initialization of the vacuum. The leak detection delay prevents the aspiration of the initial air in the tube—otherwise, the air leak sensor may detect it as a leak.

As shown in FIG. 8, the flow sensor 211 can be in communication with an indicator 212. The indicator 212 can be configured to inform the user of a characteristic of the flow parameter or flow rate. For example, the indicator 212 can be an LED light or an LED light panel, with variations in luminosity or flashing frequency that indicate the flow rate through the aspiration tubing 203. The indicator could alternatively be audible, or it could be a display on a user interface 229. The indicator 212 is shown positioned on the flow sensor 211, but in operation could be positioned anywhere within the system. The flow sensor 211 can communicate directly with the indicator 212, or via the vacuum controller 213.

The system provide for one or more manual override options, which may communicate a complete shut-off of the vacuum or aspiration flow, a scaled diminishing of the vacuum or aspiration flow, a reactivation of vacuum or aspiration flow, or a scaled increasing of the vacuum or aspiration flow. The manual commands are accepted at one or more manual inputs, such as, but not limited to, clamps, switches, buttons, sliders, knobs, pedals or a digital user interface. In some examples, a clamp 231 can be coupled to the aspiration tubing 203 to enable the practitioner to manually stop the flow of blood through the aspiration tubing 203, overriding the automated system. Alternatively or additionally, a manual override switch or button can communicate with the regulator 219 to fully open the valve to atmospheric pressure, thereby releasing the pressure in the vacuum line 207. As an alternative to a binary switch or button that fully releases the vacuum, sliders, knobs, or the like can be used to diminish or increase the vacuum force gradually. As another alternative, a foot pedal (not shown) can be activated to shut down or slow the flow either at the clamp 231, the regulator 219, or the pump 209 (or reactivate and increase the flow at any of those components). In some implementations, a manual override option can be provided at a user interface 229 (including manual or digital switches, sliders or knobs). Finally, the user has the option to turn the vacuum on and off at the vacuum pump 209, or gradually adjust its strength.

Triggering a manual override option can induce a first manual control signal to be sent from the manual input to the vacuum controller. The first manual control signal can cause the vacuum controller 213 to stop performing the step of comparing the flow parameter to the target range, or to stop the step of forming the automatic control signal, or to stop the step of sending the automatic control signal to the regulator. The vacuum controller 213 can instead send a second manual control signal to the regulator 219 based on the manual input (information from the first manual control signal). Alternatively, triggering a manual override option can send a manual control signal from the manual input directly to the regulator 219 to raise or lower the vacuum pressure in the vacuum line 207. Likewise, the manual input can be triggered to reactivate any or all of these processes.

In some implementations, the receptacle 205 can include a receptacle vent 210 in communication with the vacuum controller 213, the vacuum pump 209, the regulator 219, or with one or more of the manual inputs. Any one of the above-listed manual override actions can trigger a receptacle venting signal to be sent to the receptacle vent 210, directly or via the vacuum controller 213. The vent receives the receptacle venting signal and opens to equilibrate the pressure in the receptacle 205 with atmospheric pressure. This action eliminates residual pressure in the receptacle 205 that might otherwise cause the suction of additional blood after the manual override action. In some aspects, the venting signal may be a manual control signal sent by the vacuum controller 213 or regulator 219 upon activation of one or more manual inputs (for example, a manual command to override the vacuum system).

The clamp 231 can be coupled to tubing between the aspiration tubing 203 and the receptacle 205 and can be activated by a switch 233 for ease of use. The switch 233 can have an open configuration and a closed configuration. In the closed configuration, the switch tells the clamp 231 to close off the flow to the receptacle 205. In the open configuration, the switch 233 tells the clamp 231 to open the catheter 203 and allow blood to flow into receptacle 205. However, closure of clamp 231 can cause vacuum pressure to build up in the vacuum line 207. Opening the clamp 231 can thus cause a sudden surge and suction of blood. To avoid this, the switch 233 can be in operable communication with either the vacuum controller 213 or the regulator 219 (for example, via wiring 235). The shifting of switch 233 to the open configuration sends a surge signal to the regulator 219, either directly or via vacuum controller 213 as shown in FIG. 8. The surge signal causes the regulator to decrease the vacuum pressure in vacuum line 207, thereby reducing the surge of blood associated with opening the clamp 231. In some examples, the switch can be configured to cause a lowering of the vacuum pressure in the vacuum line 207 before releasing the clamp 231.

Some examples of the system include a user interface 229. The user interface 229 can optionally be a touch screen, or it can be in communication with a keyboard. Regardless, the user interface can be configured to accept manual input. The user interface 229 can be in communication with the vacuum controller 213 or with the regulator 219, and is configured to send manual control signals to the vacuum controller 213 or the regulator 219 responsive to the manual input. For example, the user can adjust the upper and lower limits of the target range and/or the time delay in triggering a vacuum change (for example, how long the flow rate is permitted to be at or above the upper limit before the vacuum pressure is decreased). The user interface can include a manual override button that allows the user to stop automated control and manually set the flow rate through the aspiration tubing 203. The user interface 229 can also include readouts to inform the user of the instantaneous flow rate through the aspiration tubing 203, and/or the total blood collected at receptacle 205.

Communication between the components of aspiration system 201 can take occur via any suitable communication link that facilitates data exchange between the components. Communication links can include wired, wireless, and optical links. Example communication links include, but are not limited to, a local area network (LAN), a wireless local area network (WLAN), a wide area network (WAN), a metropolitan area network (MAN), Ethernet, the internet, or any other wired, or wireless link such as WiFi, WiMax, 3G, 4G, or 5G. As shown in FIG. 8, the communication links can be formed of electrical or optical wires 215, 220, 221, 235, and 237. However, the presence of some wires in the drawing is not intended to indicate that those communication links, or any communication links, within the system must be hardwired. Any of the communication links disclosed herein can be wired or wireless in nature.

The vacuum controller 213 can advantageously be a microprocessor that operates independently of a larger computer system. For example, vacuum controller 213 can be a complex instruction set microprocessor, a reduced instruction set microprocessor, a superscalar processor, an application specific integrated circuit, or a digital signal multiprocessor. The vacuum controller 213 is configured to measure frequency from the flow parameter received from sensor 211, and includes an analog to digital converter and a digital to analog converter. Power source 239 can be any suitable power source, and can be external to the vacuum controller 213 (such as a wall outlet) or internal to the vacuum controller 213 (such as a battery).

In some implementations, power sensors 240 can be included on the pump 209 and/or the vacuum controller 213 in order to synchronize the delivery of power between the two components. That is, when one of the two components (pump 209 or vacuum controller 213) is powered off, the power sensor 240 on the other of the two components detects the power change and is automatically powered off. Likewise, when one of the two components (pump 209 or vacuum controller 213) is powered on, the other is also automatically powered on.

Figure 9:
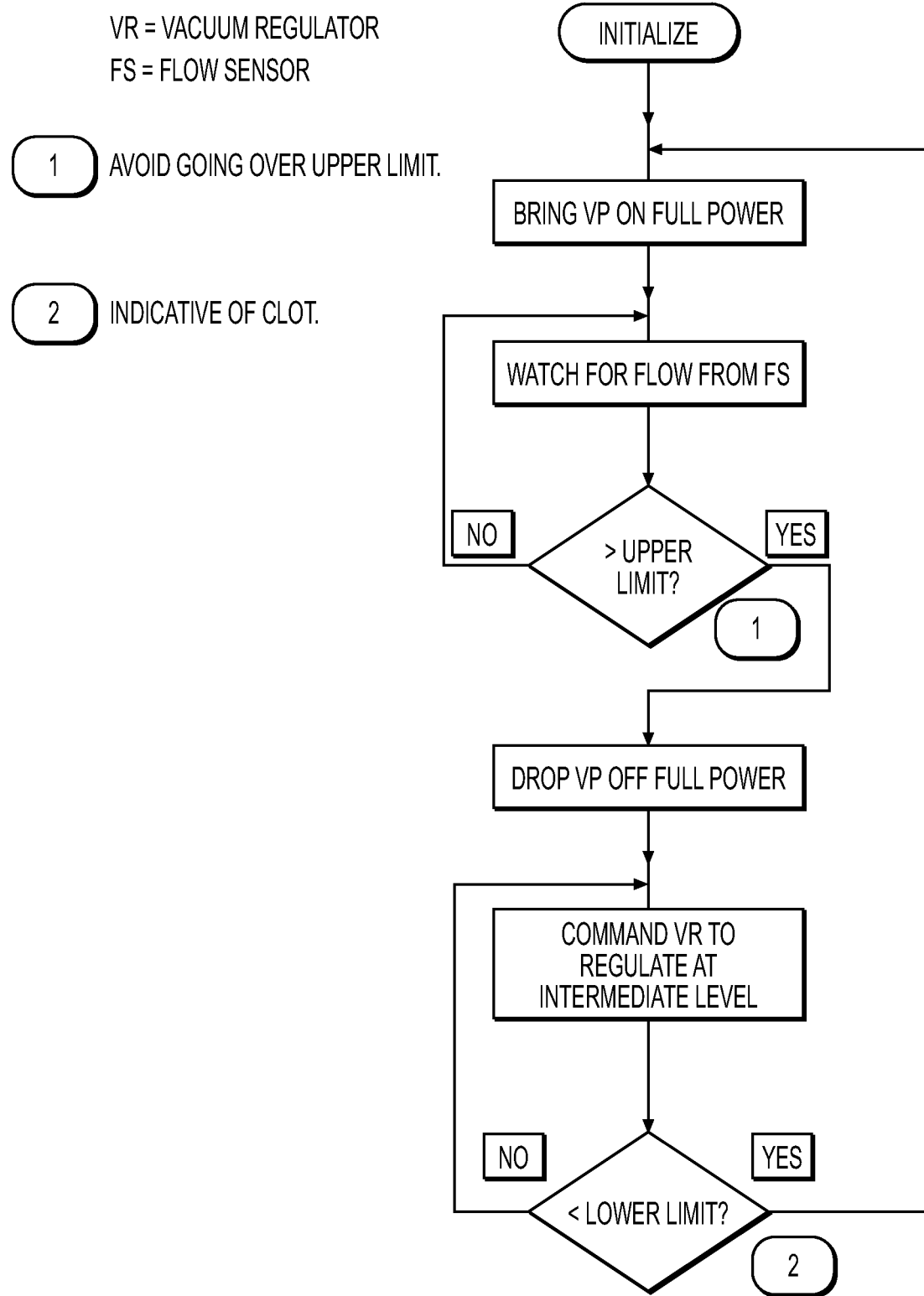
FIG. 9 is a flow chart of a method for controlling blood loss during thrombus removal.

With the basic structure of the aspiration system 201 being thusly disclosed, a greater appreciation of the construction and benefits of may be gained from the following discussion of the operation of the aspiration system 201 as shown in the flow chart at FIG. 9 and in reference to the diagram of FIG. 8. It is to be noted that this discussion is provided for illustrative purposes only. A method of controlling blood loss during thrombus removal is disclosed herein. The method includes first positioning an aspiration tubing 203 within the vascular system of a subject. The vacuum pump 209 is then initialized, or activated (either directly or via power sensor 240 which is in communication with the power supply to vacuum controller 213). The vacuum pump 209 is in fluid communication with the aspiration tubing 203. The method further includes initiating a flow of blood through an aspiration lumen 216 and measuring a flow parameter of the blood within the aspiration lumen 216 using a flow sensor 211. The method further includes receiving the flow parameter from flow sensor 211 at a vacuum controller 213. The vacuum controller 213 compares the flow parameter to a target range for the flow parameter and sends an automatic control signal to the vacuum regulator 219 based on a comparison of the flow parameter to the target range. The method further includes adjusting the vacuum pressure within the vacuum line 207 according to information stored in the automatic control signal.

In some example methods, activating a vacuum pump comprises activating the vacuum pump at full power, as shown in FIG. 9. Full vacuum power is fed to the regulator 219, which is regulated by the vacuum controller 213. When the flow exceeds the upper limit, the vacuum pump can be dropped off full power, and a finer level of intermediate control can be commanded via the regulator. The regulator can vent the system to atmospheric pressure to the extent necessary to accomplish the desired intermediate vacuum level.

The vacuum is imposed on the catheter 203 through the receptacle 205. The catheter 203 draws fluid from the patient. The flow is measured and a closed circuit loop is formed that provides controlling the desired flow with the amount of vacuum. When the flow drops below the lower limit, the vacuum controller 213 returns the vacuum pump 209 to full power and commands the regulator to fully close the system to atmospheric pressure.

Figure 10:
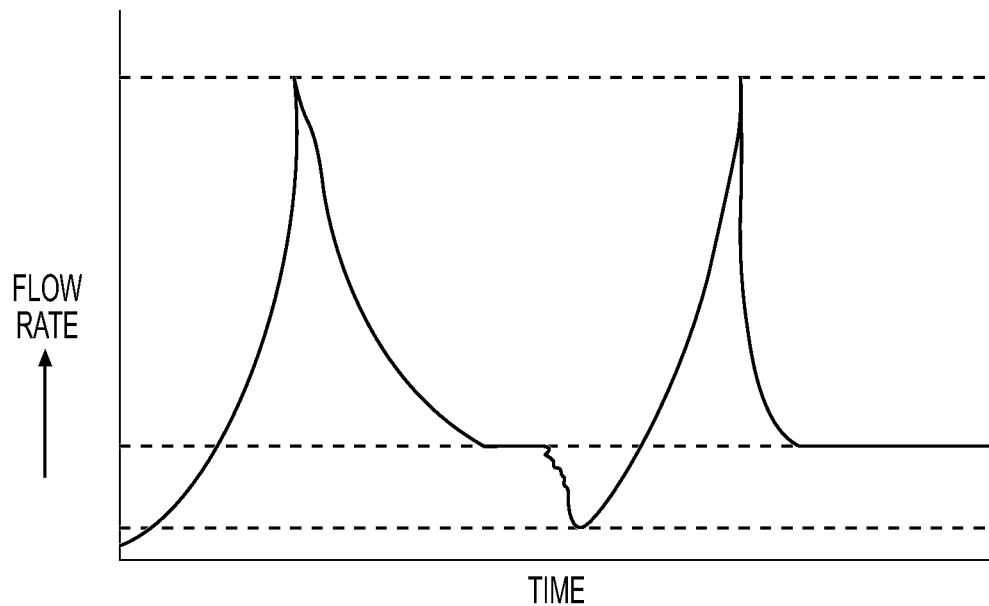
FIG. 10 is a line graph depicting a flow rate through an aspiration tubing over time.

For example, FIG. 10 shows a line graph of the flow rate in aspiration tubing 203. At initialization, the vacuum is increased to full power and flow rate reaches the first peak seen on the graph—the upper limit (uppermost dashed horizontal line). The vacuum controller 213 determines that the upper limit of the flow rate has been reached, and controller tells the regulator 219 to reduce the pressure in the vacuum line 207. The vacuum controller 213 continues to tell the regulator 219 to reduce vacuum pressure until the flow rate reaches the intermediate level (middle horizontal dashed peak). The flow rate continues at the intermediate level until it is reduced by the presence of a clot. The reduction of flow rate down to the lower limit (lowermost dashed horizontal line) causes the vacuum controller 213 to tell the regulator 219 to enable allow full vacuum power in the vacuum line 207, and the flow rate again reaches the upper limit.

Adjusting the vacuum pressure can be accomplished by decreasing the vacuum pressure upon a determination that the flow parameter is above an upper limit of the target range. In some examples, the upper limit is a flow rate of from 70 mL per minute to 130 mL per minute (including, for example, 70 mL per minute, 75 mL per minute, 80 mL per minute, 85 mL per minute, 90 mL per minute, 95 mL per minute, 100 mL per minute, 105 mL per minute, 110 mL per minute, 115 mL per minute, 120 mL per minute, 125 mL per minute, and 130 mL per minute).

In some example methods, the vacuum pressure is decreased until the measured flow parameter reaches an intermediate level flow rate of from 20 mL per minute to 50 mL per minute (including, for example, 20 mL per minute, 25 mL per minute, 30 mL per minute, 35 mL per minute, 40 mL per minute, 45 mL per minute, and 50 mL per minute).

Adjusting the vacuum pressure can be accomplished by increasing the vacuum pressure upon a determination that the flow parameter is below a lower limit of the target range. The lower limit can be, for example, from 0 mL per minute to 50 mL per minute (including, for example, 0 mL per minute, 10 mL per minute, 15 mL per minute, 20 mL per minute, 25 mL per minute, 30 mL per minute, 35 mL per minute, 40 mL per minute, 45 mL per minute, and 50 mL per minute).

Figure 11:
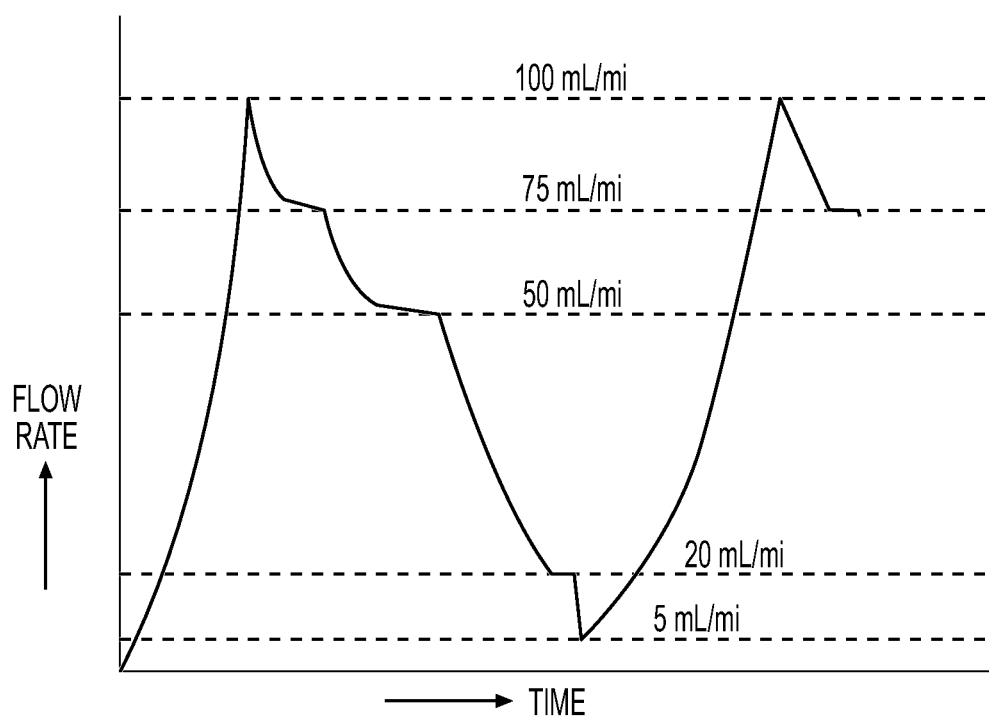
FIG. 11 is another line graph depicting a flow rate through an aspiration tubing over time.

In some implementations, decreasing or increasing the vacuum pressure can occur gradually, or in a stepwise manner, according to an aspiration program. This helps to reduce sudden surges and stops, giving the practitioner sufficient time to respond as necessary to sudden changes in flow rate. For example, FIG. 11, shows a line graph where flow rate is decreased in a step wise manner. At initialization, the vacuum is increased to full power and flow rate reaches the first peak seen on the graph—the upper limit of 100 mL per minute in this example (uppermost dashed horizontal line). The vacuum controller 213 determines that the upper limit of the flow rate has been reached, and vacuum controller 213 tells the regulator 219 to reduce the pressure in the vacuum line 207 to a first intermediate flow rate of 75 mL per minute (in this example). The vacuum controller 213 operates the regulator 219 at this first intermediate level for a specified time period and then tells the regulator to decrease the flow rate to a second intermediate level—50 mL per minute in this example. The vacuum controller 213 operates the regulator at this second intermediate level for a specified time period and then tells the regulator to decrease the flow rate to a third intermediate level—20 mL per minute in this example. The flow rate continues at the third intermediate level until it is reduced by the presence of a clot. The reduction of flow rate down to the lower limit (lowermost dashed horizontal line—5 mL per minute in this example) causes the vacuum controller 213 to tell the regulator 219 to enable allow full vacuum power in the vacuum line 207, and the flow rate again reaches the upper limit.

In some implementations, the durations of time in each of the steps of the aspiration program shown in FIG. 11 can be programmable via a manual input such as those described above. The user can set the duration of the "burst" (full vacuum power) and of each stepwise interval via a slider, a knob, a user interface, the software, or a combination thereof. The user can thus tailor the aspiration program to the procedural situation.

It should be appreciated that the logical operations described herein with respect to the various figures may be implemented (1) as a sequence of computer implemented acts or program modules (i.e., software) running on a computing device (e.g., the computing device described in FIG. 12), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 12:
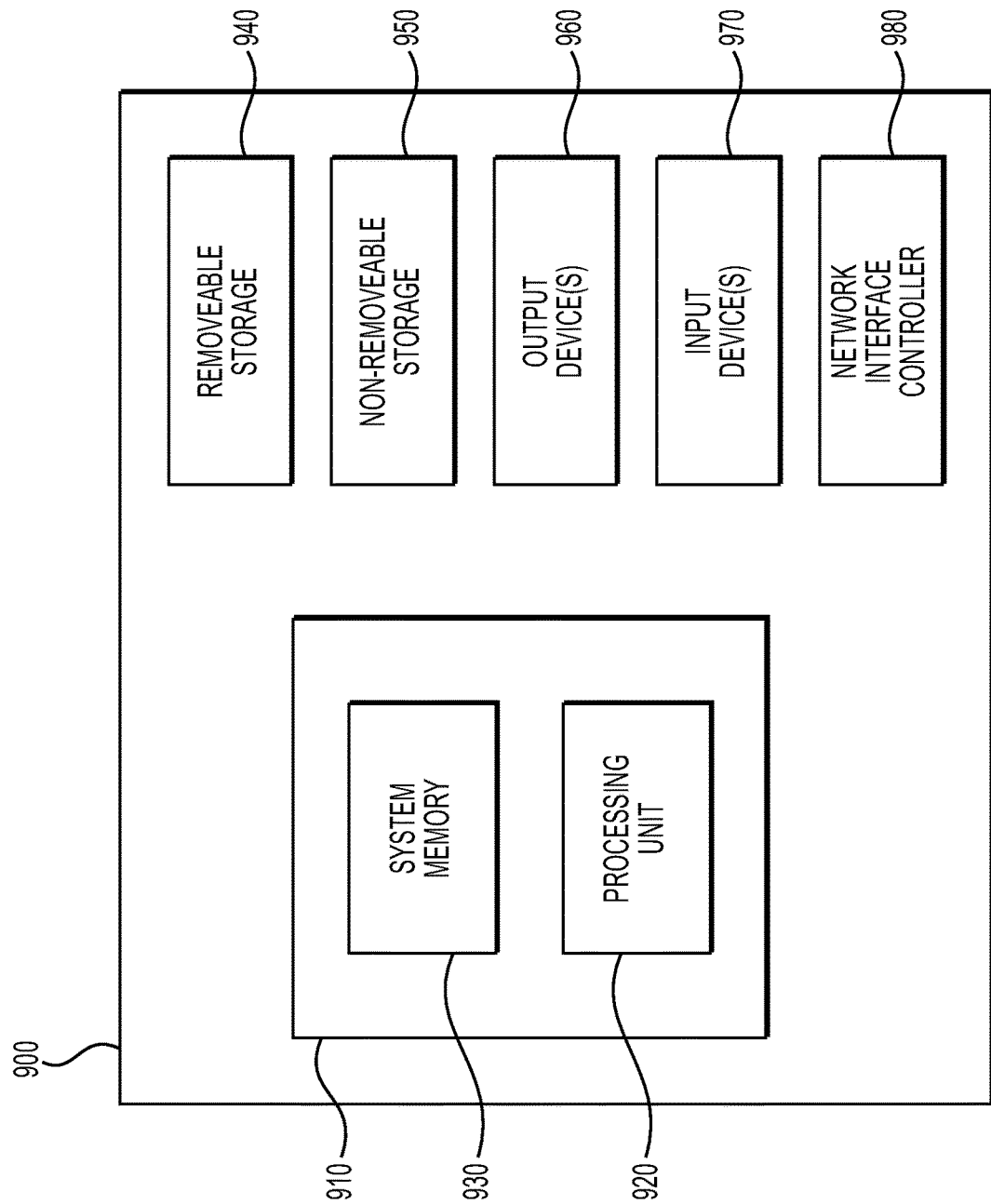
FIG. 12 is a diagram of a computing device upon which the disclosed systems may be implemented.

Referring to FIG. 12, an example computing device 900 upon which implementations of the invention may be implemented is illustrated. For example, the vacuum controller 213 may each be implemented as a computing device, such as computing device 900. It should be understood that the example computing device 900 is only one example of a suitable computing environment upon which implementations of the invention may be implemented. Optionally, the computing device 900 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In an implementation, the computing device 900 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an implementation, virtualization software may be employed by the computing device 900 to provide the functionality of a number of servers that is not directly bound to the number of computers in the computing device 900. For example, virtualization software may provide twenty virtual servers on four physical computers. In an implementation, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In its most basic configuration, computing device 900 typically includes at least one processing unit 920 and system memory 930. Depending on the exact configuration and type of computing device, system memory 930 may be volatile (such as random access memory (RAM)), non-volatile (such as read-only memory (ROM), flash memory, etc.), or some combination of the two. This most basic configuration is illustrated in FIG. 12 by dashed line 910. The processing unit 920 may be a standard programmable processor that performs arithmetic and logic operations necessary for operation of the computing device 900. While only one processing unit 920 is shown, multiple processors may be present. Thus, while instructions may be discussed as executed by a processor, the instructions may be executed simultaneously, serially, or otherwise executed by one or multiple processors. The computing device 900 may also include a bus or other communication mechanism for communicating information among various components of the computing device 900.

Computing device 900 may have additional features/functionality. For example, computing device 900 may include additional storage such as removable storage 940 and non-removable storage 950 including, but not limited to, magnetic or optical disks or tapes. Computing device 900 may also contain network connection(s) 980 that allow the device to communicate with other devices such as over the communication pathways described herein. The network connection(s) 980 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. Computing device 900 may also have input device(s) 970 such as a keyboards, keypads, switches, dials, mice, track balls, touch screens, voice recognizers, card readers, paper tape readers, or other well-known input devices. Output device(s) 960 such as a printers, video monitors, liquid crystal displays (LCDs), touch screen displays, displays, speakers, etc. may also be included. The additional devices may be connected to the bus in order to facilitate communication of data among the components of the computing device 900. All these devices are well known in the art and need not be discussed at length here.

The processing unit 920 may be configured to execute program code encoded in tangible, computer-readable media. Tangible, computer-readable media refers to any media that is capable of providing data that causes the computing device 900 (i.e., a machine) to operate in a particular fashion. Various computer-readable media may be utilized to provide instructions to the processing unit 920 for execution. Example tangible, computer-readable media may include, but is not limited to, volatile media, non-volatile media, removable media and non-removable media implemented in any method or technology for storage of information such as computer readable instructions, data structures, program modules or other data. System memory 930, removable storage 940, and non-removable storage 950 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

In an example implementation, the processing unit 920 may execute program code stored in the system memory 930. For example, the bus may carry data to the system memory 930, from which the processing unit 920 receives and executes instructions. The data received by the system memory 930 may optionally be stored on the removable storage 940 or the non-removable storage 950 before or after execution by the processing unit 920.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Implementations of the methods and systems may be described herein with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

EXAMPLE

Conventional aspiration systems operate with the vacuum being controlled with a "foot valve" by the operating physician. This is not very precise and is a distraction to the primary job of guiding the catheter. The principle of this system is to automate the process. The reader is directed to the flow chart of FIG. 9 for reference.

The system is controlled by a microprocessor controller (MC). A simple device as compared to a conventional computer and can run "stand alone". That means all it needs to run is powering it up. The program is written to be failsafe and straightforward. On power up the MC initializes and performs a test of the system and a checksum on the program. Any problem with this stops the process. The system uses a Vacuum Regulator (VR) module. It takes raw unregulated vacuum from a user supplied vacuum pump (VP). The VR can be set to deliver from full to almost zero vacuum buy the MC while the VP is set to maximum vacuum.

Another component of the system is the Flow Sensor (FS). This device measures the amount of blood flow out of the catheter. There are several available technologies for the sensor. The most straight forward and inexpensive is the impeller rotational sensor. It measures the flow by how fast an impeller spins.

An ultrasonic flow sensor works well in this application and can accurately measure the low flow rates that might indicate the possibility of a blockage caused by a blood. A small tube from the catheter is placed in a cavity on the sensor and the velocity of the flow is determined. An electrical pulse train is produced that has a frequency proportional to the flow rate that is read by the MC. The sensor is completely isolated from any liquids and can be used repeatedly, where as the rotational sensor would have to be disposed of after every procedure.

In this example, 100 mL/minute is the upper limit on the flow rate. After power on test is complete, the VR commands full vacuum. The flow can reach 100 mL/min quickly, and the MC detects that and quickly commands the VR to reduce vacuum and to control the flow by adjusting the vacuum to a midline flow rate of around 30 mL/min Without the VR, blood flow out of the catheter would be excessive.

The flow rate from 100 mL/min to 30 mL/min can be achieved in steps so that the clinician gets enough time to make necessary decisions/actions. Same delay time or stepped approach is taken for the application of full vacuum to the aspiration tubing when the flow rate falls below a lower limit of 10 ml/min (or the tip of the catheter engages a clot, in practice).

If, while the system is regulating to 30 mL/min, it drops below 10 mL/min, a blockage of the catheter has probably occurred. The system will attempt to "Clear" the blockage, usually caused by encountering a blood clot, by commanding full vacuum power from the VR. As in the beginning, when the flow hits 100 mL/min, the MC will command the VR will scale back and regulate to 30 mL/min.

The cycle repeats until the unit is shut off. Before complete shutdown, the MC commands the VR to completely release the vacuum.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The implementation was chosen and described in order to best explain the principles of the invention and the practical application, and to enable others of ordinary skill in the art to understand the invention for various implementations with various modifications as are suited to the particular use contemplated.

What is claimed is:

1. A method of controlling blood loss during thrombus removal, the method comprising:
    fluidically connecting a vacuum pump to a vacuum line and fluidically connecting the vacuum line to a receptacle for blood collection;
    fluidically connecting the receptacle for blood collection to an aspiration tubing and fluidically connecting the aspiration tubing to an aspiration catheter;
    positioning the aspiration catheter within the vascular system of a subject;
    positioning a thrombus retrieval device within the vascular system of the subject through the aspiration catheter;
    activating the vacuum pump;
    introducing a vacuum pressure and a flow of air into the vacuum line;
    introducing a vacuum pressure within the receptacle;
    initiating a flow of blood through the aspiration tubing via the vacuum pressure within the receptacle;
    collecting blood within the receptacle;
    measuring a flow parameter of the blood within the aspiration tubing using a sensor;
    receiving the flow parameter from the sensor at a vacuum controller;
    comparing the flow parameter to a target range for the flow parameter;
    sending an automatic control signal from the vacuum controller to a regulator based on a comparison of the flow parameter to the target range; and
    adjusting the vacuum pressure and flow of air within the vacuum line according to information stored in the automatic control signal, thereby adjusting the vacuum pressure within the receptacle and the flow of blood through the aspiration tubing and the aspiration catheter.

2. The method of claim 1, wherein activating a vacuum pump comprises activating the vacuum pump at full power, and the vacuum controller adjusts the vacuum pressure within the vacuum line while the vacuum pump runs at full power.

3. The method of claim 1, wherein adjusting the vacuum pressure comprises decreasing the vacuum pressure upon a determination that the flow parameter is above an upper limit of the target range.

4. The method of claim 3, wherein the upper limit is a flow rate of from 70 mL per minute to 130 mL per minute.

5. The method of claim 3, wherein decreasing the vacuum pressure comprises lowering the vacuum pressure in a stepwise manner.

6. The method of claim 3, wherein the vacuum pressure is decreased until the measured flow parameter reaches an intermediate level flow rate of 20 mL per minute to 50 mL per minute.

7. The method of claim 3, further comprising activating an aspiration program upon receipt of a manual command from one or more manual inputs in communication with the regulator, the vacuum controller, or both, wherein the aspiration program includes lowering the vacuum pressure in a stepwise manner.

8. The method of claim 1, wherein adjusting the vacuum pressure comprises increasing the vacuum pressure upon a determination that the flow parameter is below a lower limit of the target range.

9. The method of claim 8, wherein the lower limit is a flow rate of from 0 mL per minute to 50 mL per minute.

10. The method of either claim 8, wherein increasing the vacuum pressure comprises raising the vacuum pressure in a stepwise manner.

11. The method of claim 8, wherein the vacuum pressure is raised until the measured flow parameter reaches an intermediate level flow rate of 20 mL per minute to 50 mL per minute.

12. The method of claim 8, further comprising activating an aspiration program upon receipt of a manual command from one or more manual inputs in communication with the regulator, the vacuum controller, or both, wherein the aspiration program includes raising the vacuum pressure in a stepwise manner.

13. The method of claim 1, wherein adjusting the vacuum pressure within the vacuum line comprises manipulating a valve that opens the vacuum line to the atmosphere.

14. The method of claim 1, wherein measuring a flow parameter comprises measuring a flow rate.

15. The method of claim 1, further comprising using a plurality of sensors to measure one or more flow parameters of the blood at disparate points along the length of an aspiration lumen extending through the aspiration catheter and the aspiration tubing, and receiving the one or more flow parameters at the vacuum controller.

16. The method of claim 1, further comprising measuring a frequency from the flow parameter at the vacuum controller.

17. The method of claim 1, further comprising detecting air within the aspiration tubing and sending a leak signal to the regulator, the pump, or to the vacuum controller.

18. The method of claim 17, wherein detecting air within the aspiration tubing or sending a leak signal to the regulator or the pump is delayed during a vacuum initialization period.

19. The method of claim 1, further comprising accepting a manual command at a manual input and sending a first manual control signal responsive to the manual command to one or more of the vacuum controller, the regulator, or a receptacle vent.

20. The method of claim 19, further comprising stopping the vacuum controller from sending automatic control signals to the regulator.

21. The method of claim 19, further comprising forming a second manual control signal at the vacuum controller based on the first manual control signal and sending the second manual control signal to the regulator and/or receptacle vent.

22. The method of claim 19, further comprising receiving the first manual control signal at the regulator and controlling vacuum pressure within the vacuum line based on the manual control signal.

23. The method of claim 19, further comprising receiving the first manual control signal at the receptacle vent and opening or shutting the vent based on the manual control signal.

24. The method of claim 1, further comprising receiving information from the sensor at an indicator and informing a user of a characteristic of the flow parameter using the indicator.

25. The method of claim 1, further comprising shifting a switch from a closed configuration to an open configuration, wherein shifting the switch to the open configuration causes a clamp coupled to the aspiration tubing to allow fluid flow through the aspiration tubing.

26. The method of claim 25, further comprising receiving a surge protection signal upon shifting of the switch to the open configuration and decreasing the vacuum pressure upon receipt of the surge protection signal.

27. The method of claim 1, further comprising synchronizing the delivery of power between the vacuum pump and the vacuum controller.

* * * * *

UNITED STATES PATENT AND TRADEMARK OFFICE
CERTIFICATE OF CORRECTION

| | |
|---|---|
| PATENT NO. | : 11,679,195 B2 |
| APPLICATION NO. | : 17/726791 |
| DATED | : June 20, 2023 |
| INVENTOR(S) | : Ajit Nair, Christopher R. Kilgus and Ravish Sachar |

It is certified that error appears in the above-identified patent and that said Letters Patent is hereby corrected as shown below:

In the Specification

In Column 5, Line 9, delete "the" and insert -- The --
In Column 6, Line 67, delete "7A.c" and insert -- 7A --
In Column 29, Line 19, delete "domain" and insert -- domain. --
In Column 31, Line 15, delete "where as" and insert -- whereas --
In Column 31, Line 22, delete "mL/min" and insert -- mL/min. --

In the Claims

In Column 32, Line 58, Claim 10, delete "either claim" and insert -- claim --

Signed and Sealed this
Twenty-seventh Day of February, 2024

Katherine Kelly Vidal
*Director of the United States Patent and Trademark Office*